(12) United States Patent
Benjamin et al.

(10) Patent No.: US 8,546,373 B2
(45) Date of Patent: *Oct. 1, 2013

(54) METHODS OF SENSITIZING DRUG RESISTANT MICROORGANISMS USING METHYLSULFONYLMETHANE (MSM)

(75) Inventors: Rodney L. Benjamin, Vancouver, WA (US); Anthony L. Keller, Medford, OR (US); Jeffrey Varelman, Moyie Springs, ID (US)

(73) Assignee: Biogenic Innovations, LLC, Vancouver, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/458,907

(22) Filed: Apr. 27, 2012

(65) Prior Publication Data

US 2012/0264726 A1    Oct. 18, 2012

Related U.S. Application Data

(63) Continuation of application No. PCT/US2010/054871, filed on Oct. 29, 2010.

(60) Provisional application No. 61/256,935, filed on Oct. 30, 2009, provisional application No. 61/319,203, filed on Mar. 30, 2010.

(51) Int. Cl.
| | |
|---|---|
| *A61K 31/10* | (2006.01) |
| *A61K 31/165* | (2006.01) |
| *A61K 31/337* | (2006.01) |
| *A61K 31/381* | (2006.01) |
| *A61K 31/397* | (2006.01) |
| *A61P 31/04* | (2006.01) |

(52) U.S. Cl.
USPC ............................ 514/197; 514/706

(58) Field of Classification Search
USPC ..................... 514/197, 711, 706
See application file for complete search history.

(56) References Cited

U.S. PATENT DOCUMENTS

| | | | |
|---|---|---|---|
| 3,654,165 A | 4/1972 | Bryant et al. |
| 4,112,946 A | 9/1978 | Herschler |
| 4,296,130 A | 10/1981 | Herschler |
| 4,477,469 A | 10/1984 | Herschler |
| 4,514,421 A | 4/1985 | Herschler |
| 4,559,329 A | 12/1985 | Herschler |
| 4,568,547 A | 2/1986 | Herschler |
| 4,616,039 A | 10/1986 | Herschler |
| 4,863,748 A | 9/1989 | Herschler |
| 4,914,135 A | 4/1990 | Herschler |
| 4,973,605 A | 11/1990 | Herschler |
| 5,071,878 A | 12/1991 | Herschler |
| 5,753,696 A | 5/1998 | Shealy et al. |
| 6,183,758 B1 | 2/2001 | Scott |
| 6,328,987 B1 | 12/2001 | Marini |
| 6,416,772 B1 | 7/2002 | Van Engelen et al. |
| 6,426,370 B1 | 7/2002 | Hofschneider |
| 6,579,543 B1 | 6/2003 | McClung |
| 6,776,979 B2 | 8/2004 | Frager et al. |
| 7,371,407 B2 | 5/2008 | Farmer |
| 2001/0047038 A1 | 11/2001 | Moorman et al. |
| 2004/0001817 A1 | 1/2004 | Giampapa |
| 2004/0126440 A1 | 7/2004 | Frager et al. |
| 2004/0265291 A1 | 12/2004 | Drake et al. |
| 2005/0118291 A1 | 6/2005 | Wang et al. |
| 2006/0040871 A1 | 2/2006 | Levey et al. |
| 2006/0052438 A1 | 3/2006 | Ho et al. |
| 2006/0127508 A1 | 6/2006 | Larkins |
| 2006/0229262 A1 | 10/2006 | Higuchi et al. |
| 2007/0110731 A1 | 5/2007 | Riley |
| 2008/0038219 A1 | 2/2008 | Mosbaugh et al. |
| 2008/0228161 A1 | 9/2008 | Claussen et al. |
| 2008/0260708 A1 | 10/2008 | Hall |
| 2009/0017438 A1 | 1/2009 | Roy et al. |
| 2009/0017439 A1 | 1/2009 | Shimko et al. |

FOREIGN PATENT DOCUMENTS

| | | |
|---|---|---|
| CN | 1123141 | 5/1996 |
| CN | 1282577 | 2/2001 |
| EP | 2 251 003 | 11/2011 |
| WO | WO 94/05272 | 3/1994 |
| WO | WO 01/73096 | 10/2001 |
| WO | WO 2004/067013 | 8/2004 |
| WO | WO 2004/100896 | 11/2004 |
| WO | WO 2006/129149 | 12/2006 |
| WO | WO 2010/126376 | 11/2010 |

OTHER PUBLICATIONS

Enright, "The evolutionary history of methicillin-resistant *Staphylococcus aureus* (MRSA)", PNAS, May 2002, 99(11), pp. 7687-7692.*

Alekesvich et al., "Increase in the sensitivity of pathologic gum recessed microflora to streptomycin under effect of dimexide and trypsin," *Mikrobiol Zh.*, 35:766-769, 1973 (English Abstract Only; article in Ukrainian).

Andrews, "Determination of minimum inhibitory concentrations," *J. of Antimicrobial Chemotherapy*, 48:5-16, 2001.

Barrager et al., "A multicentered, open-label trial on the safety and efficacy of methylsulfonylmethane in the treatment of seasonal allergic rhinitis," *J. Alt. Complem. Med.*, 8:167-173, 2002.

Beilke et al., "Effects of dimethyl sulphoxide on the oxidative function of human neutrophils," *J. Lab. Clin. Med.*, 110:91-96, 1987.

Berry et al., "Natural Gas Odorants Desulfurization," AIChE Ann. Meet. Conf. Proc., 2004 (8 pages).

Blumenthal and Fuchs, "The clinical use of dimethyl sulfoxide on various headaches, musculosekeletal, and other general medical disorders," *Ann. N.Y. Acad. Sci.*, 141:572-585, 1967.

(Continued)

*Primary Examiner* — Renee Claytor
*Assistant Examiner* — Sahar Javanmard
(74) *Attorney, Agent, or Firm* — Klarquist Sparkman, LLP

(57) ABSTRACT

Embodiments of the invention relate generally to formulations comprising methylsulfonylmethane (MSM) and one or more therapeutic agents, and uses of such formulations to treat, inhibit and/or sensitize infectious diseases. In several embodiments, such formulations are effective to treat, inhibit and/or sensitize drug-resistant bacterial microorganisms, for example, methicillin-resistant *Staphylococcus aureus* (MRSA).

12 Claims, No Drawings

(56) References Cited

OTHER PUBLICATIONS

Bookman et al., "Effect of a topical diclofenac solution for relieving symptoms of primary osteoarthritis of the knee: a randomized controlled trial," *JAMC*, 171(4):333-338, 2004.

Borodina et al., "Dimethylsulfone as a growth substrate for novel methylotrophic species of Hyphomicrobium and Arthrobacter," *Arch. Microbiol.*, 173(5-6):425-437, 2000.

Brandt, et al., "Selective affinity of dimethyl sulphoxide (DMSO) and 2-amino-4-phenyl sulphonylbenzenesulphonamide (NSD 3004) for the large intestinal mucosa of mice," *Acta. Pharmacol. Toxicol.*, 51:173-176, 1982.

Brayton, "Dimethyl Sulfoxide (DMSO): A Review," *The Cornel Veterinarian*, 76:61-69, 1986.

Brechner et al., "Dermal anesthesia by the topical application of tetracaine base dissolved in dimethyl sulfoxide," *Ann. N.Y. Acad. Sciences*, 141:524-531, 1967.

Brien et al., "Systematic review of the nutritional supplements dimethyl sulfoxide (DMSO) and methylsulfonylmethane (MSM) in the treatment of osteoarthritis" *Osteoarthritis and Cartilage*, 16:1277-1288, 2008.

Brien et al., "Meta-analysis of the related nutritional supplements dimethyl sulfoxide and methylsulfonylmethane in the treatment of osteoarthritis of the knee," *eCAM*, doi:10.1093/ecam/nep045, 10 pages, 2009.

Brown et al., "Guidelines for the laboratory diagnosis and susceptibility testing of methicillin-resistant *Staphylococcus aureus* (MRSA)," *J. Antimicrob. Chemother.*, 56, 1000-1018, 2005.

Brown, "Clinical experience with DMSO in acute musculoskeletal conditions comparing a non-controlled series with a controlled double blind study," *Ann. N.Y. Acad. Sci.*, 141:496-505, 1967.

Dancer, "The effect of antibiotics on methicillin-resistant *Staphylococcus aureus*," *J. Antimicrob. Chemother.*, 61:246-253, 2008.

De Lencastre et al., "Antibiotic resistant *Staphylococcus aureus*: a paradigm of adaptive power," *Curr. Opin. Microbiol.*, 10, 428-435, 2007.

Debi et al., "The role of MSM in knee osteoarthritis: a double blind, randomized prospective study," *Osteoarthritis and Cartilage*, 15:427, 2008.

Demos et al., "Dimethyl Sulfoxide in Musculoskeletal Disorders," *Ann. N.Y. Acad. Sci.*, 141:517-523, 1967.

Eberhardt et al., "DMSO in patients with activated gonarthrosis," *Fortschr. Med.*, 113:446-450, 1995 (Abstract only).

Evans et al., "Dimethylsulfoxide (DMSO) blocks conduction in peripheral nerve C fibers: a possible mechanism of analgesia," *Neurosci. Lett.*, 150:145-148, 1984.

Feldman et al., "In vivo and in vitro effects of dimethyl sulfoxide on streptomycin-sensitive and -resistant *Escherichia coli*," *Ann. N.Y. Acad. Sci.*, 243:269-277, 1975.

Gerhards and Gibian, "The metabolism of dimethyl sulfoxide and its metabolic effects in man and animals," *Ann. N.Y. Acad. Sci.*, 141:65-76, 1967.

Glasser, "Dimethylsulfoxide (DMSO) "resensibilization" as potential chemotherapy for opportunistic mycobacterial disease," *Am. Rev. Respir. Dis.*, 118:969-970, 1978.

Gorbach and Samtsov, "Therapeutic possibilities of inhalation of rifampicin with dimexide in phthisiopulmonolgy," *Probl. Tuberk.*, 3:34-36, 1991 (in Russian, with English Abstract).

Gupta, "New delivery systems for topical nutraceutical (nutracosmetic) and cosmeceutical formulations," *Business Briefing: Global Cosmetic Manufacturing*, 1-5, 2004.

Haigler and Spring, "Comparison of the analgesic effect of dimethyl sulfoxide and morphine," *Ann. N.Y. Acad. Sci.*, 411:19-27, 1983.

Hasegawa, Suppressive effects of methylsulfonylmethane (MSM) on type II collagen induced arthritis in DBA/iJ mice, *J. Pharmacol. Ther.*, 32:421-427, 2004.

Horvath et. al., "Toxicity of methylsulfonylmethane in rats," *Food Chem. Toxicol.*, 40:1459-62, 2002.

Hucker, et al., "Studies on the absorption, excretion and metabolism of dimethylsulfoxide (DMSO) in man," *J. Pharmacol. Exp. Therap.*, 155:309-317, 1967.

Jacob and Appleton, "MSM: The Definitive Guide: A comprehensive review of the science and therapeutics of Methylsulfonylmethane," *Freedom Press*, Topanga, CA, 2003 (51 pages).

Jacob and Herschler, "Dimethyl sulfoxide after twenty years," *Ann. N.Y. Acad. Sci.*, 411:14-18, 1983.

Jacob and Herschler, "Pharmacology of DMSO," *Cryobiology*, 23:14-27, 1986.

Jacob et al., "The miracle of MSM: the natural solution for pain," pp. 51-97; pp. 122-132; pp. 139-144; pp. 191-214, *Berkley Trade*, 1999.

Jacob and Wood, "Dimethyl sulfoxide (DMSO): toxicology, pharmacology, and clinical experience," *Am. J. Surg.*, 114:414-426, 1967.

Jagannath et al., "Enhancement of drug susceptibility of multi-drug resistant strains of *Mycobacterium tuberculosis* by ethambutol and dimethyl sulphoxide," *J. Antimicrob. Chemother.*, 35(3):381-390, 1995.

Jimenez and Willkens, "Dimethyl Sulphoxide: a perspective of its use in rheumatic diseases," *J. Lab. Clin. Med.*, 100:489-500, 1982.

John and Laudahn, "Clinical experiences with the topical application of DMSO in orthopedic diseases: evaluation of 4180 cases," *Ann. N.Y. Acad. Sci.*, 141:506-516, 1967.

Karlson and Ulrich, "Stability of rifampin in dimethylsulfoxide," *Appl. Microbiol.*, 18:692-693, 1969.

Kim et al., "Efficacy of methylsulfonylmethane (MSM) in osteoarthritis pain of the knee: a pilot clinical trial," *OsteoArthritis and Cartilage*, 14:286-294, 2006.

Knowles "Clinical experience with DMSO in small animal practice," *Ann. N.Y. Acad. Sci.*, 141:478-483, 1967.

Koenen et al., "Percutaneous therapy of activated osteoarthritis of the knee—comparison between DMSO and diclofenac," *Therapiestudie*, 38:534-538, 1996 (in German, with English Abstract).

Layman and Jacob, "The absorption, metabolism, and excretion of dimethyl sulfoxide by rhesus monkeys" *Life Sciences*, 37:2431-2437, 1985.

Lee et al., "Evaluation of genotoxicity on plant derived dietary sulfur," *J. Microbiol. Biotech.*, 16:817-820, 2006.

Liubinets and Kruk, "Applying dimexide in treatment of endobronchitis in patients with destructive forms of pulmonary tuberculosis," *Zh Ushn Nos Gorl. Bolesn.*, 29:68-71, 1969 (in Russian, with English Abstract).

Lockie and Norcross, "A clinical study on the effects of dimethyl sulfoxide in 103 patients with acute and chronic musculoskeletal injuries and inflammations," *Ann. N.Y. Acad. Sci.*, 141:599-602, 1967.

Lu et al., "A mouse model for the evaluation of pathogenesis and immunity to Influenza A (H5N1) viruses isolated from humans," *J. Virol.*, 73:5903-5911, 1999.

Magnuson et al., Pharmacokinetics and distribution of [35S]-methylsulfonylmethane following oral administration in rats, *J. Agri. Food Chem.*, 55:2033-2038, 2006.

Magnuson et al., "Oral development toxicity of Methylsulfonylmethane in rats," *Food Chem. Toxicol.*, 45:977-984, 2007.

Martin and Hauthal, *Dimethyl Sulfoxide*, New York: John Wiley & Sons, 1971 (chapter 12, 21 pages).

Matsumoto, "Clinical trials of dimethyl sulfoxide in rheumatoid arthritis patients in Japan," *Ann. N.Y. Acad. Sci.*, 141:560-568, 1967.

Mitinskaia et al., "BCG vaccination and increasing the effectiveness of treatment of post-vaccination complications by the use of fifampicin and dimexide," *Probl. Tuberk*, 5:4-7, 1994 (in Russian, with English Abstract).

Mohamaddi and O'Mara, "Unusual patient odor interfering with care," *Ann. Emerg. Med.*, 27:391-392, 1996.

Müller and Urbanczik, "Influence of dimethyl Sulfoxide (DMSO) on restoring sensitivity of mycobacterial strains resistant to chemotherapeutic compounds," *J. Antimicrob. Chemother.* 5:326-327, 1979.

Muravyev et al., "Effect of dimethyl sulfoxide and dimethyl sulfone on a destructive preocess (sic) in the joints of mice with spontaneous arthritis," *Patol Fiziol Eksp*, 2:37-39, 1991 (in Russian, with English Abstract).

Nash and Steingrube, "In vitro drug sensitivity of *M. Avium*—Intracellulare complex in the presence and absence of dimethyl sulphoxide," *Microbios.*, 35:71-78, 1982.

Oshima et al., "The effect of distilled methylsulfonylmethane (MSM) on human chondrocytes in vitro," *Osteoarthritis and Cartilage*, 15:213, 2007.

Ostojic et al., "Laboratory testing of cabin air filters for the removal of reduced-sulfur odors," *New Engine Design and Automotive Filtration SAE Special Publications*, 1362:41-58, 1998.

Paul, "Interval therapy with dimethyl sulfoxide," *Ann. N.Y. Acad. Sci.*, 141:586-598, 1967.

Paulus, "FDA advisory committee meeting: methotrexate; guidelines for the clinical evaluation of anti-inflammatory drugs: DMSO in scleroderma," *Arthritis heum.*, 29:1289-1290, 1986.

Penrod et al., "Dimethyl sulfoxide for incisional pain after thoracotomy: Preliminary Report," *Ann. N.Y. Acad. Sci.*, 141:493-495, 1967.

Pottz et al., "The effect of dimethyl Sulfoxide (DMSO) on antibiotic sensitivity of a group of medically important microorganisms: preliminary report," *Ann. N.Y. Acad. Sci.*, 141:261-272, 1967.

Pratt et al., "A study of the absorption of OptiMSM (methylsulfonylmethane) in horses," *Proc. 17th Equine Nutr. Physiol. Soc.*, pp. 141-142, 2001.

Ropek et al., "Effects of dimethyl sulfoxide on Tubercle bacilli resistant to INH," *Gruzlica.*, 39:738-741, 1971.

Seibert, "DMSO and other combatants against bacteria isolated from leukemia and cancer patients," *Ann. N.Y. Acad. Sci.*, 141:175-201, 1967.

Shanmugam et al. "The effects of methylsulfonylmethane on hair growth promotion of magnesium ascorbyl phosphate for the treatment of alopecia," *Biomolecules and Ther.*, 17:241-248, 2009.

Shaklee Health Network, "Methyl Sulfonyl Methane," retrieved from the internet on Dec. 16, 2010; URL:http://content.nhiondemand.com/shp/monoVMN.asp?objID=100028.

Simon et al., "Efficacy and safety of topical diclofenac containing dimethyl sulfoxide (DMSO) compared with those of topical placebo, DMSO vehicle and oral diclofenac for knee osteoarthritis," *Pain*, 143:238-245, 2009.

Smith et al., "Anti-inflammatory effects of topically applied dimethylsulphoxide gel on endotoxin-induced synovitis in horses," *Am. J. Vet. Res.*, 59:1149-52, 1998.

Steinberg, "The employment of DMSO as an anti-inflammatory agent and steroid transporter in diversified clinical diseases," *Ann. N.Y. Acad. Sci.*, 141:532-550, 1967.

Sturenberg, "Rapid detection of methicillin-resistant *Staphylococcus aureus* directly from clinical samples: methods, effectiveness and cost considerations," *GMS*, 7:1-19, 2009.

Szmant, "Physical properties of dimethyl sulfoxide and its function in biological systems," *Ann. N.Y. Acad. Sci.*, 243:20-23, 1975.

Szydlowska, "Studies on the role of dimethylsulfoxide in resensibilization of antibiotic-resistant bacterial strains," *Arch. Immunol. Ther. Exp. (Warsz)*, 20:193-202, 1972.

Szydlowska, "In vitro and in vivo Studies on the Role of Dimethylsulfoxide (DMSO) in Resensibilization of Bacterial Strains Resistant to Antibiotics and Chemotherapeutic Agents," *Abl. Bakt. Hyg.*, 239:270-274, 1977.

Szydlowska and Pawlowska, "Comparative studies on the influence of dimethylsulfoxide (DMSO) on reversion to sensitivity to isonicotinic acid hydrazide (INH) and rifampicin (RMP) in resistant strains of tubercle bacilli," *Arch. Immunol. Ther. Exp. (Warsz)*, 24:575-577, 1976.

Szydlowska and Pawlowska, "In vivo studies on reversion to sensitivity of INH-resistant tubercle bacilli under the influence of dimethylsulfoxide (DMSO)," *Arch. Immunol. Ther. Exp. (Warsz).*, 22(4):559-561, 1974.

Teigland and Saurino, "Clinical evaluation of dimethyl sulfoxide in equine applications," *Ann. N.Y. Acad. Sci.*, 141:471-477, 1967.

Tiews et al., "Metabolism and excretion of dimethyl sulfoxide in cows and calves after topical and parenteral application," *Ann. N.Y. Acad. Sci.*, 243:139-150, 1975.

Usha and Naidu, "Randomized, double-blind, parallel, placebo-controlled study of oral glucosamine, methylsulfonylmethane and their combination in osteoarthritis," *Clin. Drug. Invest.*, 24:353-363, 2004.

Vignes, "Dimethyl Sulfoxide: a superior solvent underutilized because of a safety myth," Semiconductor Safety Association Annual Meeting, Arlington, VA, Apr. 25-28, 2000.

Vuopala et al., "The analgesic action of DMSO ointment in arthrosis," *Acta. Rheum. Scand.*, 17:57-60, 1971.

Wierzbicki, "Homocysteine and cardiovascular disease: a review of the evidence" *Diabetes and Vascular Disease Research*, 4:143-149, 2007.

Williams et al., "Metabolism of dimethyl sulfide, dimethyl sulfoxide and dimethyl sulfone in the rabbit," *Arch. Biochem. Biophys.*, 117:84-87, 1966.

Windrum et al., "Variation in dimethyl sulfoxide use in stem cell transplantation: a survey of EBMT centres," *Bone Marrow Transplantation.*, 36:601-603, 2005.

Wong et al., "Absorption, excretion and biotransformation of dimethyl sulfoxide in man and miniature pigs after topical application as an 80% gel," *J. Invest. Dermatol.*, 56:44-48, 1971.

Wood and Wood, "Pharmacologic and biochemical consideration of dimethyl sulfoxide," *Ann. N.Y. Acad. Sci.*, 143, 7-19, 1975.

Zhang et al., "Assessment of methylsulfonylmethane as a permeability enhancer for regional EDTA chelation therapy," *Drug Delivery*, 16:243-248, 2009.

Zuckner et al., "Local application of dimethyl sulfoxide and DMSO combined with triacinolone acetonide in rheumatoid arthritis," *Ann. N.Y. Acad. Sci.*, 141:555-559, 1967.

"Additive Free MSM Methylsulfonylmethane," http://www.worldimagenaturals.com/products/msm/indes.php, 5 pages, downloaded Aug. 18, 2010.

"AloeCalm™ All-Natural and Organic Body Lotion," http://www.acne-answrs.org/products/aloe-calm.html, 6 pages, downloaded Jul. 5, 2010.

"How to Flush the Toxins out of Your Body from the Swine or H1N1 Flu Shot," http://www.ehow.com, 3 pages, downloaded Aug. 18, 2010.

"Methylsulfonylmethane," http://en.wikipedia.org/wiki/Methylsulfonylmethane, 5 pages, downloaded Jul. 5, 2010.

"MSM—MethylSulfonylMethane," http://pages.prodigy.net/naturedoctor/msm.html, 6 pages, downloaded Jul. 5, 2010.

"Sulfur (MSM): A Basic Essential Nutrient Needed, Now, More than Ever Before," http://www.all-natuarl.com/msm.html, 7 pages, downloaded Aug. 11, 2010.

International Search Report issued by the Australian Patent Office on Jan. 31, 2011 in related parent application PCT/US2010/054837 (3 pages).

Written Opinion issued by the Australian Patent Office on Jan. 31, 2011 in related parent application PCT/US2010/054837 (4 pages).

International Search Report issued by the Australian Patent Office on Jan. 14, 2011 in related parent application PCT/US2010/054871 (3 pages).

Written Opinion issued by the Australian Patent Office on Jan. 14, 2011 in related parent application PCT/US2010/054871 (9 pages).

"Can MSM (Methylsulfonylmethane) Save Your Skin?" http://blog.pharmacymix.com/can-msm-methylsulfonylmethane-save-your-skin, downloaded Apr. 15, 2013 (5 pages).

Kulshrestha et al., "Inhibition of Bacteria by Some Volatile and Non-Volatile Compounds Associated with Milk. III. *Staphylococcus aureus*," *J. Milk Food Technol.*, 37(11):545-550, 1974 (6 pages).

Lovett et al., "La rocacée un problème qui fait rougir," *LaMédecin due Quebec* 40:35-39, 2005 (reference in French).

Chinese Office Action dated Mar. 27, 2013, for Chinese Patent Application No. 201080060119.8, with English-language translation (10 pages).

Extended European Search Report dated Mar. 26, 2013, for European Patent Application No. 10827568.6 (10 pages).

International Search Report issued by the Australian Patent Office on Jan. 31, 2011 in PCT/US2010/054837 (3 pages).

Written Opinion issued by the Australian Patent Office on Jan. 31, 2011 in PCT/US2010/054837 (4 pages).

International Search Report issued by the Australian Patent Office on Dec. 10, 2010 in related parent application PCT/US2010/054845 (4 pages).

Written Opinion issued by the Australian Patent Office on Dec. 10, 2010 in PCT/US2010/054845 (8 pages).

* cited by examiner

METHODS OF SENSITIZING DRUG RESISTANT MICROORGANISMS USING METHYLSULFONYLMETHANE (MSM)

RELATED APPLICATIONS

This is a continuation of PCT/US2010/054871, filed Oct. 29, 2010, which was published in English under PCT Article 21(2), and claims the benefit of U.S. Provisional Application Nos. 61/256,935, filed Oct. 30, 2009, and 61/319,203, filed Mar. 30, 2010. The disclosure of each of these patent documents is expressly incorporated by reference herein.

BACKGROUND

1. Field of the Invention

Embodiments of the invention relate generally to formulations comprising dimethyl sulfoxide (DMSO) alone or in combination with methylsulfonylmethane (MSM) to treat infectious diseases. Certain embodiments relate to sensitizing drug-resistant microbes to drugs. Several formulations disclosed herein are useful for treating drug-resistant tuberculosis.

2. Description of the Related Art

Infectious diseases are diseases caused by pathogenic microbial agents, including viruses, bacteria, fungi, parasites, and prions, among others. The pathogenic agents may be primary or opportunistic pathogens. Primary pathogens cause infection as a direct result of their virulence, while opportunistic pathogens typically require a compromised host defense system to produce an infection. Examples of common infectious diseases include HIV/AIDS, measles, tetanus, tuberculosis, malaria, upper and lower respiratory infections, and hepatitis. While modern medicine has reduced the prevalence of many infectious diseases, particularly in developed countries, they still account for a large degree of morbidity and mortality.

Tuberculosis, malaria, HIV/AIDS, and diarrhoeal diseases are the leading killers among the infectious diseases. Tuberculosis (*tubercle bacillus*) is caused by mycobacteria, primarily *Mycobacterium tuberculosis*. Tuberculosis primarily infiltrates the lungs (pulmonary tuberculosis), but has also been documented as affecting the central nervous system, the lymphatic system, and the circulatory system, among others. Other mycobacteria may also cause tuberculosis, for example, *Mycobacterium bovis*, *Mycobacterium africanum*, *Mycobacterium canetti*, and *Mycobacterium microti*. However, these species are less common in humans.

Despite certain improvements in medical treatment for infectious diseases (antibiotics and vaccines), there remain many obstacles to reducing the mortality caused by these diseases. A primary issue is the emergence and spread of drug resistant pathogens. Tuberculosis and other infectious diseases have shown resistance to first-line drugs. In some instances, resistance has progressed to require a change to more expensive second or third-line agents. Evolution of pathogenic microorganisms is expected due to the selective pressure of drug therapy. However, resistance is exacerbated by several factors, including abuse, underuse or misuse of antimicrobials, poor patient compliance, and poor quality of available drugs.

Dimethyl sulfoxide (DMSO; $(CH_3)_2(SO)$) is a polar, aprotic solvent widely used as a solvent. It is frequently used in various chemical and biological reactions and as a cryoprotectant for cell storage. The strong unpleasant odor of DMSO (or metabolites), among other side effects, has adversely impacted the use of DMSO in medical applications.

Methylsulfonylmethane (MSM; $(CH3)_2SO_2$)), also known as dimethyl sulfone, is an organosulfur compound that is a metabolite of DMSO and certain sulfur-containing amino acids. MSM has been marketed primarily as a dietary supplement.

SUMMARY

There exists a need for an effective and easily administered therapy against infectious diseases, particularly those that are developing or have developed some degree of antimicrobial resistance.

Tuberculosis classically presents as a chronic cough with blood-tinged sputum, fever, night sweats, and weight loss. Tuberculosis may also infect other organ systems, leading to a diverse set of symptoms. Diagnosis of tuberculosis is typically achieved through radiology, tuberculin skin test, blood tests, as well as microscopic examination and microbiological culture of bodily fluids. Current tuberculosis treatment requires long courses of multiple antibiotics. One course of treatment for tuberculosis is isoniazid, rifampicin, pyrazinamide, and ethambutol for about two months, followed by only isoniazid and rifampicin for a further four months. The patient is considered cured at six months (although there is still a relapse rate of 2 to 3%). Latent tuberculosis therapy involves six to nine months of isoniazid alone.

Drug-resistant tuberculosis includes tuberculosis that is resistant to at least one anti-tuberculosis drug. Multidrug-resistant tuberculosis (MDR tuberculosis) includes tuberculosis that is resistant to more than one first line anti-tuberculosis drug.

In several embodiments, formulations comprising DMSO alone or DMSO in combination with MSM, and a therapeutic agent are provided to treat tuberculosis, including drug-resistant tuberculosis.

In several embodiments, formulations comprising DMSO alone or in combination with MSM are provided as an inhalant to treat drug-resistant tuberculosis. In some embodiments, formulations comprising DMSO alone or in combination with MSM are formulated as solids, while in several other embodiments, formulations comprising DMSO and MSM are formulated as liquids. In some embodiments, the formulations are consumed orally to treat drug-resistant tuberculosis, while in some other embodiments, the formulations are applied topically. In several embodiments, drug-resistant diseases other than tuberculosis are treated with formulations comprising DMSO alone or in combination with MSM.

In yet other embodiments, non-drug-resistant diseases are treated with formulations comprising DMSO alone or DMSO in combination with MSM. In such embodiments, DMSO or a combination of DMSO and MSM is combined with a therapeutic agent to enhance the effects of the therapeutic agent.

In several embodiments, subjects with drug-resistant tuberculosis are treated with a DMSO formulation, an MSM formulation, or combination of DMSO and MSM, together with isoniazid, rifampicin, pyrazinamide, and ethambutol for a time period (e.g., two weeks-two months), then isoniazid and rifampicin alone for another time period (e.g., four weeks-four months). In some embodiments, subjects with drug-resistant tuberculosis are treated with a DMSO formulation, alone or in combination with MSM, together with isoniazid, rifampicin, pyrazinamide, and/or ethambutol. In one embodiment, DMSO alone or in combination with MSM formulations sensitize drug-resistant tuberculosis to antibiotics, and therefore isoniazid, rifampicin, pyrazinamide, and/or ethambutol become lethal to sensitized tuberculosis bacteria. In other embodiments, subjects with drug-resistant tuberculosis are treated with a DMSO formulation, alone or in combination with MSM, together with one or more of the following: isoniazid, rifampicin, pyrazinamide, ethambutol, lamprene, mycobutin, seromycin, streptomycin, myambutol, priftin and rifamate In several embodiments, a system for treating drug-resistant tuberculosis is provided. In one embodiment, the system comprises a therapeutic agent and DMSO alone, or a combination of DMSO and MSM. The concentration of the DMSO and/or MSM ranges from about 15% to about 95% in a total volume of about two to about six milliliters. The therapeutic agent is selected from one or more compounds selected from the group consisting of: isoniazid, rifampicin, pyraziamide, and ethambutol. In one embodiment, the system includes an inhalant device, wherein the inhalant device is constructed from a material adapted for contacting DMSO and/or MSM and wherein the inhalant device is configured for administering the formulation to a subject. The inhalant device is configured to deliver the formulation to directly contact drug-resistant tuberculosis bacteria in the subject's lung tissue. In one embodiment, the DMSO and/or MSM sensitizes the drug-resistant tuberculosis bacteria to at least one of isoniazid, rifampicin, pyraziamide, and ethambutol to generate sensitized tuberculosis bacteria. The sensitized tuberculosis bacteria are lethally inhibited by exposure to least one of isoniazid, rifampicin, pyraziamide, and ethambutol.

In several embodiments, the invention comprises a method for treating drug-resistant tuberculosis. In one embodiment, the method comprises providing a formulation comprising a therapeutic agent and DMSO alone, or a combination of DMSO and MSM. In one embodiment, the concentration of DMSO and/or MSM ranges from about 15% to about 95% in a total volume of about two to about six milliliters. In one embodiment, the therapeutic agent is selected from one or more compounds selected from the group consisting of: isoniazid, rifampicin, pyraziamide, and ethambutol. In some embodiments, the method further includes providing an inhalant device and administering the formulation via the inhalant device to a subject having drug-resistant tuberculosis. The inhalant device is configured to deliver the formulation to directly contact drug-resistant tuberculosis bacteria in the subject's lung tissue. The drug-resistant tuberculosis bacteria are sensitized (with the DMSO) to at least one of isoniazid, rifampicin, pyraziamide, and ethambutol to generate sensitized tuberculosis bacteria, and lethally inhibited by at least one of isoniazid, rifampicin, pyraziamide, and ethambutol. In one embodiment, a method of treating drug-resistant tuberculosis in the field is provided. In one embodiment, a test for tuberculosis is performed within hours of seeing a subject, a test for INH and RRP is given within hours, the subject is treated with DMSO alone or in combination with MSM (e.g., intravenously), and then treated with a inhaled formulation of DMSO alone or in combination with MSM, provided with mask and trained to use an inhalant device in the field. Methods of treating drug-resistant diseases other than tuberculosis with DMSO alone or in combination with MSM are also provided according to several embodiments.

In several embodiments, the invention comprises a formulation for sensitizing drug-resistant microorganisms to a therapeutic agent. In one embodiment, the formulation comprises a therapeutic agent and DMSO alone or a combination of DMSO and MSM. The concentration of the DMSO and/or MSM ranges from about 15% to about 95% in a total volume or weight of the formulation. The DMSO or combination of DMSO and MSM is configured for contacting a drug-resistant microbe, wherein the drug-resistant microbe is resistant to the therapeutic agent. After contact with the DMSO or combination of DMSO and MSM the drug-resistant microbes are sensitized to the therapeutic agent and are transformed into sensitized microbes, wherein the sensitized microbes are inhibited by the therapeutic agent. The drug-resistant microorganism contacted with DMSO or a combination of DMSO and MSM includes, but is not limited to, tuberculosis, malaria, MRSA and *streptococcus*.

In some embodiments, the inhalant device is an inhaler, nebulizer or ventilator. According to several embodiments, the inhalant device is constructed from a material adapted for contacting DMSO and/or MSM without degrading into the subject's airway, trachea, bronchial tubes, or lung tissue, or without rupturing. In one embodiment, the formulation is pre-dosed in the inhalant device.

In some embodiments, the total formulation volume is about 2-8 ml, e.g., about 3 ml for an inhaler or 7 ml for a nebulizer. According to some embodiments, the formulations described herein also comprise urea. Urea may be provided in a dose about 1 mg to about 10 grams or higher in several embodiments. In one embodiment, formulations disclosed herein are configured for delivery at least three times daily.

In one embodiment, the formulation comprises a daily dose of: rifampicin in an amount ranging from about 500 mg to about 700 mg, isoniazid in an amount ranging from about 200 mg to about 400 mg, pyrazinamide in an amount ranging from about 2.0 g to about 3.0 g, and ethambutol in an amount ranging from about 1.0 g to about 2.0 g. In another embodiment, the formulation comprises a total daily dose or a daily dose per kg of body weight of: rifampicin in an amount ranging from about 1 mg to about 100000 mg, isoniazid in an amount ranging from about 2 mg to about 10000 mg, pyrazinamide in an amount ranging from about 0.02 g to about 10.0 g, and ethambutol in an amount ranging from about 0.01 g to about 10.0 g. In one embodiment, the formulation comprises a daily dose of about 600 mg rifampicin, 300 mg isoniazid, 2.4 g pyrazinamide, and 1.2 g ethambutol. Streptomycin or other therapeutic agents are included in several embodiments. In one embodiment, streptomycin is provided in a total daily dose or a daily dose per kg of body weight of about 10 mg to about 200 g.

A system according to any one of the preceding claims, further comprising a pretreatment composition, wherein the pretreatment composition comprises about 50 mg to about 60 mg DMSO and is configured for intravenous administration to the subject.

In several embodiments, wherein the inhalant device is configured to generate particles of the formulation that range in size from about 0.5 micron (μm) to about 5 μm.

In one embodiment, the invention comprises a kit for treating drug-resistant tuberculosis, comprising: a system according to any one of the embodiments described herein; and instructions for administering the formulation via the inhalant device at least three times daily. The kit may also include a mask, a battery charger and/or a battery pack.

DETAILED DESCRIPTION

In several embodiments described herein, formulations comprising DMSO alone or in combination with MSM are provided. In several embodiments, such formulations are used to treat tuberculosis, including drug-resistant tuberculosis. Despite the increasing prevalence of drug-resistant pathogenic microbes, several embodiments of the formulations disclosed herein are unexpectedly effective in treating drug-resistant bacteria or other microbes. Other drug-resistant pathogenic microbes are also treated by DMSO alone, or a combination of DMSO and MSM, together with a therapeutic agent.

Formulations according to several embodiments herein include DMSO alone (e.g., (i) without MSM or any other active ingredient; (ii) without MSM but with one or more active ingredients; and/or (iii) without MSM and with or without one or more inactive ingredients). Formulations according to several embodiments herein include DMSO in combination with MSM, wherein the combination may or may not include one or more inactive or active ingredients.

In several embodiments, the combination of DMSO and MSM allows a lower concentration of DMSO and/or MSM to be used. In other embodiment, the use of DMSO alone or in combination with MSM reduces the minimum efficacious concentration of other constituents of the formulation, thereby also reducing side effects from those constituents. For example, in one embodiment, the addition of DMSO, MSM or DMSO and MSM will permit a reduced dosage of antibiotics, or other antimicrobial, to achieve comparable or enhanced therapeutic effects.

In several embodiments, formulations comprising DMSO alone or in combination with MSM sensitize drug-resistant tuberculosis to drugs. In one embodiment, formulations comprising DMSO alone or in combination with MSM partially or fully reverse the drug-resistant nature of bacterial strains, including tuberculosis.

In one embodiment, DMSO or combination of DMSO and MSM enhances the permeability of bacteria (or other microbes), thus enhancing the effectiveness of the antibiotic (or other therapeutic agent). In another embodiment, DMSO or combination of DMSO and MSM serves as a carrier that carries an antibiotic (or other therapeutic agent) into the cell. In a further embodiment, DMSO creates permanent or temporary pores on or in the cell to enhance delivery of drugs. In other embodiments, the use of MSM in combination with DMSO enhances the effectiveness of DMSO. In some embodiments, MSM reduces the concentration of DMSO required, thereby reducing concomitant side-effects. In further embodiments, MSM in combination with DMSO enhances the permeability of antibiotics and/or serves as a carrier for antibiotics (or other therapeutic agents).

In several embodiments, formulations comprising DMSO or DMSO in combination with MSM and at least one therapeutic agent lower the concentration of DMSO, MSM, and/or the therapeutic agent needed to effectively treat one or more types of infection. In one embodiment, a formulation comprising DMSO alone or in combination with MSM sensitizes the bacteria (whether drug-resistant or not) to antibiotics. Thus, such a formulation: (i) reduces the dose of antibiotic needed; (ii) reduces the treatment time; (iii) reduces the number of different antibiotics needed, and/or (iv) makes an antibiotic effective. Accordingly, undesired side effects associated with antibiotics may be reduced in several embodiments, including liver damage, kidney damage, ocular defects, hyperuricemia, thrombocytopenia, leukopenia, and neutropenia. In one embodiment, a DMSO formulation or combination of DMSO with MSM formulation sensitizes drug-resistant tuberculosis to isoniazid, rifampicin, pyrazinamide, and/or ethambutol. In additional embodiments, DMSO alone or in combination with MSM enhances the effects of isoniazid, rifampicin, pyrazinamide, and/or ethambutol on non drug-resistant tuberculosis. Pulmonary and extra-pulmonary tuberculosis are treated according to several embodiments.

Many infections lead to local inflammation (or even inflammation of a large area of tissue around the site of infection). In some embodiments, DMSO alone or in combination with MSM works synergistically with therapeutic agents to reduce inflammation to a greater degree than DMSO, MSM or the agent alone.

As used herein, the term "therapeutic agents" shall be given its ordinary meaning and shall include an agent or agents that ameliorate or cure an illness or symptoms of an illness. Therapeutic agents shall include, but not be limited to, analgesics, anti-inflammatory agents, antimicrobial agents (such as anti-parasitic, antifungal, antiviral, and antibiotic agents), and combinations thereof.

In several embodiments, DMSO and MSM in a single formulation with a therapeutic agent act synergistically to reduce the amount of DMSO needed to achieve efficacious amounts of therapeutic agent delivery to a target site of infection. In some embodiments, MSM enhances the penetrant effect of DMSO, allowing a therapeutic agent to reach a target area of infection at an increased concentration (or reduced time frame). Thus, in some such embodiments, the synergy between MSM and DMSO reduce the side effects associated with DMSO administration, which include an unpleasant odor post administration, nausea, diarrhea, and skin/throat irritation, among others.

In still other embodiments, DMSO and MSM in a single formulation with a therapeutic agent act synergistically to reduce the amount of therapeutic agent needed to effectively treat an infection. For example, many antibiotics have an established minimum inhibitory concentration (MIC) at which they are effective in reducing or killing certain bacteria (e.g., associated with tuberculosis). In some embodiments, a formulation comprising DMSO and MSM and a sub-MIC concentration of an antibiotic is equally or more effective at reducing or killing such bacteria as compared to the antibiotic alone at MIC levels. In other embodiments, a formulation comprising DMSO, MSM and an antibiotic are more effective at reducing or eliminating bacteria associated with tuberculosis from a site of infection as compared to the antibiotic alone. In several embodiments, formulations disclosed herein augment treatment of multiple drug-resistant tuberculosis. In one embodiment, formulations disclosed herein sensitize *mycobacterium tuberculosis* strains in vitro, in macrophages and in vivo to drugs. In one embodiment, a formulation comprising DMSO and ethambutol sensitizes bacteria to drugs other than ethambutol. In some embodiments, formulations comprising DMSO enhance the sensitivity or susceptibility to drugs such as sub-MIC concentrations of ethambutol, isoniazid, rifampicin, and streptomycin by about 2-fold to about 100-fold. Unlike prior reports, concentrations of DMSO greater than 50% are particularly advantageous in some embodiments. *Enhancement of drug susceptibility of multi-drug resistant strains of Mycobacterium tuberculosis by ethambutol and dimethyl sulphoxide*. Jagannath et al. Journal of Antimicrobial Chemotherapy (1995) 35, 381-390, herein incorporated by reference.

In some embodiments, DMSO alone or in combination with MSM allow antibiotics (or other therapeutic agents) to penetrate lung tissue infected with tuberculosis. In one embodiment, DMSO alone or in combination with MSM: (i) allow antibiotics to reach deeper levels of tuberculosis infected tissue; (ii) allow direct contact of tuberculosis infected tissue; (iii) lengthen the exposure time of the antibiotic to the tuberculosis infected tissue; and/or (iv) decrease the time to achieve a desired antibiotic effect. In one embodiment, DMSO alone or in combination with MSM achieves one or more of these desired effects through use as an inhalant, wherein the inhalant additionally comprises one or more antibiotics or other therapeutic agents.

In several embodiments, the combined use of MSM reduces or eliminates the odor normally associated with DMSO. This is surprisingly beneficial in several embodiments because practitioners have avoided using DMSO in high concentrations (or in any amount) because of its unpleasant odor.

In some embodiments, DMSO alone or DMSO in combination with MSM formulations comprise antiparasitic agents that are effective in treating infections caused by parasites, such as nematodes, cestodes, trematodes, protozoa, or amoebae.

In some embodiments, DMSO alone or DMSO in combination with MSM formulations comprise antifungal agents that are effective in treating fungal infections, such as those caused by ringworm, candidiasis, and *Cryptococcus* (cryptococcal meningitis, for example).

In some embodiments, DMSO alone or DMSO in combination with MSM formulations comprise antiviral agents that are effective in treating viral infections. In some embodiments, specific classes of antiviral agents are used to treat infections caused by a particular type of virus. In some embodiments, agents that target HIV, herpes viruses, hepatitis B or C viruses, and influenza viruses are used.

In several embodiments, DMSO alone or DMSO in combination with MSM formulations comprise antibiotics that are effective in treating bacterial infections by, for example, inhibiting bacterial growth, metabolism, proliferation, activity and/or function. In some embodiments, bacteriostatic antibiotics are used, while in other embodiments, bactericidal antibiotics are used. In still other embodiments, both bacteriostatic and bactericidal antibiotics are incorporated into a single formulation comprising DMSO and/or MSM. In some embodiments, antibiotics of one or more classes are incorporated into a formulation comprising DMSO alone or DMSO in combination with MSM. In certain embodiments, a formulation includes one or more of an: aminoglycoside, ansamycin, carbacephem, carbapenem, cephalosporin ($1^{st}$, $2^{nd}$, $3^{rd}$, $4^{th}$, or $5^{th}$ generation), glycopeptides, macrolide, monobactam, penicillin, polypeptide, quinolone, sulfonamide, tetracycline, and the like.

In some embodiments, specific diseases are targeted by incorporating specific antibiotics into a formulation comprising DMSO alone or DMSO in combination with MSM. For example, macrolides, such as azithromycin or erythromycin are incorporated into formulations used to treat respiratory or mycoplasmal infections. Likewise, penicillins, such as amoxicillin or oxacillin are incorporated into formulations used to treat a broad range of streptococcal infections.

In still other embodiments, specific disease-causing microorganisms are targeted by the specific antibiotics incorporated into a formulation comprising DMSO alone or DMSO in combination with MSM. For example, aminoglycosides, such as neomycin are incorporated into formulations used to treat *Escherichia coli* infections. In several embodiments, antibiotics typically used to combat microbial infections are used. In certain embodiments, antibiotics including, but not limited to, isoniazid, rifampicin, pyraziamide, and ethambutol are incorporated into formulations comprising one or more of DMSO and MSM, and are used to treat tuberculosis, including drug-resistant tuberculosis.

In several embodiments of the invention, formulations comprising DMSO, MSM and one or more of the following therapeutic agents: rifampicin, isoniazid, pyrazinamide, and ethambutol are provided. In other embodiments, formulations comprising DMSO and at least one of rifampicin, isoniazid, pyrazinamide, and ethambutol are provided. In several embodiments, formulations comprising DMSO alone, or in combination with MSM in combination with rifampicin, isoniazid, pyrazinamide, and ethambutol are provided to treat tuberculosis, including drug-resistant tuberculosis.

In some embodiments, rifampicin is provided in a total daily dose ranging from about 400 mg to about 800 mg per day. In some embodiments, rifampicin is provided in a total daily dose ranging from about 500 mg to about 700 mg per day, while in still other embodiments, it is provided in a total daily dose ranging from about 550 to about 650 mg per day, including 560, 570, 580, 590, 600, 610, 620, 630, and 640 mg per day. In some embodiments, higher or lower quantities may be used.

In some embodiments, isoniazid is provided in a total daily dose ranging from about 100 mg to about 500 mg per day. In some embodiments, isoniazid is provided in a total daily dose ranging from about 200 mg to about 400 mg per day, while in still other embodiments, it is provided in a total daily dose ranging from about 250 mg to about 350 mg per day, including 260, 270, 280, 290, 300, 310, 320, 330, and 340 mg per day. In some embodiments, higher or lower quantities may be used.

In some embodiments, pyrazinamide is provided in a total daily dose ranging from about 1.0 to about 4.0 g per day. In some embodiments, pyrazinamide is provided in a total daily dose ranging from about 2.0 to about 3.0 g per day, while in still other embodiments, it is provided in a total daily dose ranging from about 2.0 to 2.5 g per day, including 2.1, 2.2, 2.3, and 2.4 g. In some embodiments, higher or lower quantities may be used.

In some embodiments, ethambutol is provided in a total daily dose ranging from about 0.5 to about 2.5 g per day. In some embodiments, ethambutol is provided in a total daily dose ranging from about 1.0 to 2.0 g per day, while in still other embodiments, it is provided in a total daily dose ranging from about 1.0 to about 1.5 g per day, including 1.1, 1.2, 1.3, and 1.4 g. In some embodiments, higher or lower quantities may be used.

In some embodiments, DMSO alone or in combination with MSM is used to pretreat a patient suffering from an infectious disease, such as drug-resistant tuberculosis. In some embodiments, the dose of DMSO alone or in combination with MSM used to pretreat patients ranges from about 10% to 50% weight to volume. In some embodiments, the pretreatment DMSO alone or in combination with MSM dose ranges from about 20% to about 40%, from about 25% to 35%, including 26, 27, 28, 29, 30, 31, 32, 33, and 34%. In some embodiments, about 50% to about 100% DMSO and/or MSM is used. In several embodiments, pretreatment with DMSO and/or MSM enhances the ability of an antibiotic to inhibit tuberculosis associated bacterial activity and/or sensitizes a drug-resistant strain to a drug that was previously ineffective.

In some embodiments, a formulation is prepared wherein antimicrobials are dissolved in DMSO alone or in combination with MSM prior to administration. This is particularly advantageous in certain embodiments because the antimicrobial and DMSO (and optionally MSM) can be administered to a subject via inhalation to treat tuberculosis. Inhalants, according to some embodiments, provide direct access of the DMSO alone or in combination with MSM to infected lung tissue to sensitize bacterial cells to the antibiotic to treat tuberculosis.

In one embodiment, an inhalant is provided to target the site of infection (e.g., lungs) of several infectious diseases, such as tuberculosis. In some such embodiments, the inhalant device comprises a nebulizer. In other embodiments, an inhaler is used. In some embodiments, a pressurized metereddose inhaler is used, and the formulation is inhaled in liquid aerosol form. In other embodiments, dry powder inhalers are used, and the formulation is inhaled in a powder aerosol form. In several embodiments, oral, intravenous, intramuscular, or subcutaneous administration is used in addition to or instead of inhalant therapy.

The ability to administer antimicrobial agents as an inhalant (e.g., in a powder aerosol form) with DMSO alone or DMSO in combination with MSM is especially advantageous in some embodiments because it allows for increased shelf-stability and pre-packaged dosages. This is particularly helpful for individuals in underdeveloped or developing nations who do not have regular access to healthcare facilities. Entire courses of treatment can be provided to an affected subject in a single visit to a healthcare practitioner without the need for a hospital stay or repeat visits. In several embodiments, formulations disclosed herein are suitable for self-administration (e.g., through inhalant devices) and are therefore especially appropriate for patients with limited access to healthcare.

In certain embodiments, the total volume of inhaled DMSO alone or in combination with MSM is about 2-8 ml. In some embodiments, the total volume of inhaled DMSO alone or in combination with MSM is about 2 ml to about 4 ml. In some embodiments, the total volume of inhaled DMSO alone or in combination with MSM is about 6 ml to about 8 ml. In still other embodiments, the total volume of inhaled DMSO alone or in combination with MSM is about 3 ml to about 7 ml, including 4, 5, and 6 ml. Thus, in some embodiments, the concentration of DMSO administered via inhalation ranges from about 65% to about 95%, including 70, 75, 80, 85, 86, 87, 88, 89, 90, 91, 92, 93, and 94%, and overlapping ranges thereof.

In several embodiments, MSM is included with the inhaled DMSO and antimicrobial compounds. In certain embodiments, the amount of inhaled MSM used in combination with DMSO ranges from about 0.01% by weight to about 70% by weight. In other embodiments, the inhaled formulation contains between about 0.01% and 10% MSM (used in combination with DMSO) by weight. Other embodiments contain between about 10 and 20% MSM, about 20-30% MSM, about 30-40% MSM, about 40-50% MSM, about 50-60% MSM, or about 60-70% MSM including 60, 61, 62, 63, 64, 65, 66, 67, 68, 69, and 70% MSM, and overlapping ranges thereof (each used in combination with DMSO). Still other embodiments comprise a formulation containing about 7 and 15% MSM, about 15-25% MSM, about 25-35% MSM, about 35-45% MSM, about 55-60% MSM, about 60-65% MSM, or about 65-70% MSM (each used in combination with DMSO). Thus, in some embodiments of the inhaled formulation containing MSM, the concentration of DMSO administered ranges from about 50% to about 95%, including 55, 60, 65, 70, 75, 80, 85, 86, 87, 88, 89, 90, 91, 92, 93, and 94%, and overlapping ranges thereof.

In several embodiments, the use of MSM reduces the amount of DMSO needed to achieve a comparable effect and/or enhances the efficacy of DMSO by at least 10%, 25%, 50%, 100%, 2-fold, 3-fold, 5-fold, 10-fold, 50-fold, or 100-fold. In other embodiments, the use of MSM reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold. In further embodiments, the use of DMSO reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold. In still other embodiments, the use of DMSO and MSM reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold as compared to DMSO or MSM alone and/or the therapeutic agent alone.

In several embodiments, a pretreatment formulation comprising DMSO, alone or in combination with MSM, is administered to a subject intravenously, intramuscularly, topically or orally to enhance the effects of an inhalant therapy comprising DMSO alone or in combination with MSM with therapeutic agents, such as antibiotics. The pretreatment with DMSO, alone or in combination with MSM, enhances the inhalant's therapeutic effects by at least 10%, 25%, 50%, 100%, 2-fold, 3-fold, 5-fold, 10-fold, 50-fold, or 100-fold.

In several embodiments, subjects having drug-resistant tuberculosis are treated with a formulation comprising, consisting or consisting essentially of DMSO, alone or in combination with MSM, and one or more therapeutic agents, such as antibiotics. In some embodiments, the formulation additionally includes other therapeutics agents, carriers or excipients. In one embodiment, the formulation additionally includes arginine, vitamin D, antioxidants, macrolides, linezolid, thioacetazone, thioridazine, or combinations thereof.

Delivery Devices

DMSO readily disrupts the integrity of many materials (particularly plastics and polymers used in manufacturing disposable medical equipment). Accordingly, several embodiments of the invention comprise devices to facilitate the storage and administration of DMSO. In some embodiments, DMSO is stored in glass bottles and administered through non-reactive tubing. In other embodiments, inhalant devices are specially designed to be DMSO resistant. In some embodiments, portions of the inhalant devices are disposable or replaceable. According to several embodiments, formulations comprising DMSO are manufactured, stored and/or administered using materials and devices disclosed in U.S. patent application Ser. No. 12/066,480, which is the National Phase entry of International Application No.: PCT/US06/35499, filed Sep. 11, 2006, which is herein incorporated by reference in its entirety.

In certain embodiments, the delivery device delivers droplets or particles of the inhaled formulation of a size capable of reaching the bronchioles of the patient's lungs. In some embodiments, activation of the delivery device is synchronized with a patient's breathing rhythm to carry the formulation to the bronchioles. Inhalant therapy according to one embodiment, enables more direct administration the inhaled formulation to infected pulmonary target tissues. Direct targeting is advantageous in some embodiments because it allows for reduction of the amount of antimicrobial compounds incorporated into the formulation while maintaining or improving efficacy of the formulation against infectious microorganisms. In other embodiments, direct administration increases the efficacy of a given antimicrobial regime against one or more drug-resistant strains of microorganism. Direct targeting, according to other embodiments, minimizes side effects by minimizing contact with non-targeted tissue.

The small droplet or particle size that are provided according to some embodiments reduces the volume of DMSO alone or DMSO in combination with MSM that is administered as compared to traditional ventilator therapy. For example, in one embodiment, the use of an inhalant device (e.g., nebulizer) will be efficacious with about 6 mg to about 25 mg DMSO and/or MSM daily, as compared to 50-100 mg daily when administered through certain other pathways. Reducing DMSO is beneficial in some embodiments because it reduces undesired side effects and odor. In other embodiments, higher amounts of DMSO are used and tolerated.

In several embodiments, the addition of MSM unexpectedly reduces the unpleasant odor normally experienced with DMSO use. For example, in certain embodiments, DMSO and MSM formulations produce no perceptible odor after use. In some other embodiments having DMSO concentrations approaching or exceeding 50%, the combination with MSM in the formulation reduces or eliminates the DMSO-based odor. Such a result is unexpected, given that DMSO use is normally associated with a strong unpleasant odor.

In some embodiments, the use of DMSO alone or DMSO in combination with MSM with one or more therapeutic agents (such as antibiotics) permits the manufacture and/or administration of small droplets or particle sizes, thereby reducing the irritation of the mucosa of the mouth and throat, as the droplets or particles travel more deeply into the lungs of the patient. In some embodiments, the depth of travel of the droplets or particles increases the concentration of the dissolved antibiotics in the patient's lungs.

In several embodiments, DMSO alone or in combination with MSM formulations are combined with therapeutic agents (such as antibiotics) and provided as an aerosol to deliver locally-active drugs to the respiratory system to treat tuberculosis or other respiratory diseases. In one embodiment, the lower airways are contacted (or contacted exclusively) with the formulation. In other embodiments, the formulation is used to systemically treat illnesses. For systemically-active drugs, the aerosol particles are sized to reach the alveolar surface in peripheral areas of the lung.

In some embodiments, the use of DMSO alone or in combination with MSM formulations comprising a therapeutic agent (such as an antibiotic) is particularly advantageous because it provides rapid onset of action. In one embodiment, inhalation delivery provides a large absorption area of the lung. For locally acting drugs, the onset of action is immediate in some embodiments. Systemically-active inhaled formulations, according to some embodiments, reach the blood stream quickly. Inhalation therapy provides a therapeutic effect within about 1-90 minutes in some embodiments, including about 10 to 20 minutes, about 20 to 30 minutes, about 30 to 40 minutes, about 40 to 50 minutes, about 50 to 60 minutes, about 60 to 70 minutes, about 70 to 80 minutes, about 80 to 90 minutes, and overlapping ranges thereof. In one embodiment, DMSO alone or in combination with MSM enhances the bioavailability of the therapeutic agent. In a further embodiment, DMSO alone or in combination with MSM reduces the degradation of the therapeutic agent. In another embodiment, aerosol formulations disclosed herein reduce the gastrointestinal side effects or skin irritation that may occur with oral or topical treatment.

In several embodiments, inhalant particles are sized to minimize the deposit of those particles by inertial impact into the upper airways without reaching the site of action. In several embodiments, the particles are sized to minimize deposit in the mouth and throat, thereby minimizing swallowing and undesired local or systemic side effects. In several embodiments, the particles are smaller than 2, 5 or 10 µm. In one embodiment, the particles are about 3-5 µm and are transported into the bifurcations and smaller airways of the bronchii and bronchioles. In another embodiment, the particles are less than 3 µm and follow the airflow into the alveoli. In several embodiments, the use of DMSO alone or in combination with MSM allows for optimizing the particle size of the therapeutic agent. Thus, diseases such as tuberculosis can be more effectively treated. Moreover, in several embodiments, the use of DMSO alone or in combination with MSM sensitizes drug-resistant tuberculosis to antibiotics and/or renders drug-sensitive microbes more sensitive to an effective therapeutic agent.

In several embodiments, DMSO alone or in combination with MSM forms a solution, mixture, emulsion, suspension, or other suitable combination with the therapeutic agent. In one embodiment, homogenization, sonication, high shear fluid processing, or other mechanical methods are used to combine the therapeutic agent with the DMSO or combination of DMSO and MSM. In other embodiments, the therapeutic agent dissolves readily in DMSO. Unlike other strong solvents, DMSO is not harmful to lung tissue. Thus, DMSO is especially advantageous in some embodiments because it can both dissolve the therapeutic agent and deliver said agent without damaging lung tissue. In some embodiments, DMSO dissolves at least 50%, 75%, 90%, 95%, or 99% of the therapeutic agent, and in one embodiment, is able to prevent undesired precipitation of the therapeutic agent.

In some embodiments, sprays, gels or wipes comprising DMSO, alone or in combination with MSM, and antibacterial agents are provided for sanitizing medical equipment, surfaces and the body to minimize the spread of infectious disease.

Treatment of Drug-Resistant Diseases

In several embodiments, a formulation comprising DMSO alone or in combination with MSM and antimicrobial agents are used as a treatment for an infectious disease, including drug-resistant organisms.

In certain embodiments, formulations of DMSO or a combination of DMSO and MSM disclosed herein are effective to treat various infectious diseases including, but not limited to, *acinetobacter* infection, actinomycosis, Adenovirus infection, African sleeping sickness (African trypanosomiasis), AIDS, amebiasis, anaplasmosis, Anthrax, *Arcanobacterium haemolyticum* infection, Argentine hemorrhagic fever, *ascariasis*, aspergillosis, astrovirus infection, babesiosis, *Bacillus cereus* infection, bacterial pneumonia, bacterial vaginosis (BV), *Bacteroides* infection, balantidiasis, Baylisascaris infection, BK virus infection, black piedra, *Blastocystis* hominis infection, blastomycosis, Bolivian hemorrhagic fever, *Borrelia* infection, botulism, Brazilian hemorrhagic fever, brucellosis, *Burkholderia* infection, Calicivirus infection, campylobacteriosis, candidiasis (moniliasis; thrush), cat-scratch disease, cellulitis, Chagas disease, chancroid, chickenpox, chlamydia, *Chlamydophila pneumoniae* infection, cholera, chromoblastomycosis, clonorchiasis, *clostridium difficile* infection, coccidioidomycosis, Colorado tick fever, common cold, Creutzfeldt-Jacob disease, Crimean-Congo hemorrhagic fever, cryptococcosis, cryptosporidiosis, cutaneous larva migrans (CLM), cyclosporiasis, cysticercosis, cytomegalovirus infection, dengue fever, dientamoebiasis, diphtheria, diphyllobothriasis, dracunculiasis, Ebola hemorrhagic fever, echinococcosis, ehrlichiosis, enterobiasis (Pinworm infection), *Enterococcus* infection, enterovirus infection, epidemic typhus, erythema infectiosum, exanthem subitum, fasciolopsiasis, fasciolosis, fatal familial insomnia (FFI), filariasis, food poisoning, free-living amebic infection, *Fusobacterium* infection, gas gangrene (Clostridial myonecrosis), geotrichosis, Gerstmann-Strüssler-Scheinker syndrome (GSS), giardiasis, glanders, gnathostomiasis, gonorrhea, granuloma inguinale (Donovanosis), Group A streptococcal infection, Group B streptococcal infection, *Haemophilus influenzae* infection, hand, foot and mouth disease (HFMD), Hantavirus, *Helicobacter pylori* infection, hemolytic-uremic syndrome (HUS), hemorrhagic fever with renal syndrome (HFRS), Hepatitis A, B, C, D, or E, herpes simplex, histoplasmosis, hookworm infection, human bocavirus infection, Hhman ewingii ehrlichiosis, human granulocytic anaplasmosis (HGA), human metapneumovirus infection, human monocytic ehrlichiosis, human papillomavirus (HPV) infection, human parainfluenza virus infection, and hymenolepiasis.

In certain embodiments, formulations of DMSO or a combination of DMSO and MSM disclosed herein are also effective in treating one or more of the following infectious diseases, Epstein-Barr Virus Infectious Mononucleosis (Mono), Influenza (flu), Isosporiasis, Kawasaki disease, Keratitis, *Kingella kingae* infection, Kuru, Lassa fever, Legionellosis, Leishmaniasis, Leprosy, Leptospirosis, Listeriosis, Lyme disease, Lymphatic filariasis, Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis Microsporidia, *Molluscum contagiosum* (MC), Mumps, Murine typhus, *Mycoplasma* pneumonia, Mycetoma, Myiasis, Neonatal conjunctivitis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, Pneumocystis pneumonia (PCP), Pneumonia, Poliomyelitis, Poliovirus, Primary amoebic meningoencephalitis (PAM), Progressive multifocal leukoencephalopathy, Psittacosis, Q fever, Rabies, Rat-bite fever, Respiratory syncytial virus, Rhinosporidiosis, Rhinovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis, Shingles (Herpes zoster), Smallpox, Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans (OLM)), Toxocariasis (Visceral Larva Migrans (VLM)), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White piedra, *Yersinia pseudotuberculosis* infection, Yersiniosis, Yellow fever, and Zygomycosis.

In several embodiments, formulations of DMSO or a combination of DMSO and MSM disclosed herein are particularly effective in treating one or more infectious diseases that are resistant to drug therapies. In addition to those infectious diseases listed above, which may already be or may become drug resistant in the future, certain embodiments using DMSO or a combination of DMSO and MSM are effective in treating, among others, drug resistant: tuberculosis, measles, tetanus, malaria, upper and lower respiratory infections, hepatitis, typhoid fever, vancomycin/glycopeptide-intermediate *Staphylococcus aureus* infection, vancomycin-resistant enterococci, methicillin-resistant *Staphylococcus aureus* (MRSA), and *streptococcus pneumoniae*.

In some embodiments, treatment of an infectious disease comprises the pretreatment of a patient with DMSO, followed by the administration of a formulation comprising DMSO and antimicrobial agents. In other embodiments, treatment of an infectious disease comprises the pretreatment of a patient with DMSO, followed by the administration of a formulation comprising DMSO, MSM, and antimicrobial agents. In some embodiments, DMSO pretreatment is administered intravenously via a fast drip IV catheter. In other embodiments, the DMSO is given in a bolus IV injection. In yet other embodiments, pretreatment with DMSO is not performed. Pretreatment compositions additionally include MSM, a therapeutic agent or a combination thereof in some embodiments.

In several embodiments, formulations comprising DMSO and antimicrobial agents, or DMSO, MSM and antimicrobial agents are administered orally, intravenously, intramuscularly, or subcutaneously. However, as the site of infection of several infectious diseases, including tuberculosis, is the lungs, in some embodiments, formulations are administered by inhalation. In some such embodiments, the inhalant means comprises a nebulizer. In other embodiments, an inhaler is used.

As discussed above, the use of a DMSO alone or in combination with MSM formulation comprising an antimicrobial formulation in a nebulizer or an inhaler provides particular advantages in several embodiments. In certain embodiments, the dose of antimicrobial compounds that reduce or eliminate microorganisms is reduced compared to using the same antimicrobial compounds alone. In other embodiments, the delivery of a formulation as described herein, via a nebulizer or inhaler, is more effective at reducing or eliminating infectious microorganisms as compared to intravenous, intramuscular, oral, or standard ventilator based therapy. In addition, the use of nebulizers or inhalers in some embodiments provides the improved ability to bring treatment to patients in geographical areas that are not amenable to standard treatment techniques requiring hospitalization time. The efficacious therapy and improved portability realized with some embodiments is especially beneficial given the long-felt, but unmet need for such a type of therapy.

In several embodiments, subjects are pretreated with DMSO using intravenous DMSO by fast drip within, e.g., a ten minute period (or less). In one embodiment, DMSO will be provided in glass bottles with proprietary non-reactive tubing. Subjects will then receive antibiotics dissolved in DMSO in 3 ml doses through an inhaler or mouth spray three times a day with meals. In one embodiment, DMSO pretreatment is provided in the range of about 25 mg to about 75 mg (e.g., 30 mg, 40 mg, 50 mg, 60 mg, 70 mg) in 200 ml 5% dextrose and water. In one embodiment, 56 mg DMSO in 200 ml 5% dextrose and water is provided. In one embodiment, the following antibiotics are provided: rifampicin, isoniazid, pyrazinamide, and ethambutol. In one embodiment, about 600 mg rifampicin, 300 mg isoniazid, 2.4 g pyrazinamide, and 1.2 g ethambutol are administered per day, through an inhaler/nebulizer or mouth spray delivered in 3 ml dosages, three times daily. In one embodiment, the antibiotics are combined with DMSO for delivery via inhalation, with or without the pretreatment with DMSO. Pretreatment with MSM is also provided in several embodiments. Intravenous pretreatment of DMSO, or a combination of DMSO and MSM is provided in some embodiments. Pretreatment formulation may also comprises therapeutic agents.

In several embodiments, therapeutic effects are obtained within two weeks of treatment, within two months of treatment, and/or within six months of treatments. Other therapeutic windows are also provided.

In several embodiments, subjects who test positive for the presence of the *M. tuberculosis* complex and are resistant one or more antibiotics (such as rifampicin and isoniazid) are identified and treated. After treatment with a formulation comprising DMSO alone or in combination with MSM and rifampicin, isoniazid, pyrazinamide, and ethambutol, the treated subjects will show a negative sputum mycobacterial culture and/or show improvement in one or more of the following symptoms: coughing, chest pain, shortness of breath, labored breathing, weight loss, fatigue, fever, night sweats, chills, and loss of appetite. In other embodiments, treated subjects will show a greater reduction in *M. tuberculosis* colonies resulting from the culturing of sputum samples as compared to control group patients who are not provided DMSO alone or a combination of DMSO and MSM. In some embodiments, in addition to, or in instead of, reducing the number of *M. tuberculosis* colonies cultured from sputum samples, the overall health and robustness of the resulting colonies is reduced, indicating potentially reduced severity of infection as well as demonstrating that the DMSO-based treatment is negatively impacting the *M. tuberculosis*.

In some embodiments, patients pretreated with DMSO show better improvement than those treated with inhalant DMSO and antibiotics without intravenous DMSO pretreatment. In some embodiments, patients treated with DMSO with inhalant DMSO and antibiotics show better improvement than those treated with antibiotics alone. In several embodiments, the addition of MSM to the formulation containing DMSO enhances the therapeutic effects or reduces side effects. In one embodiment, MSM is used alone as a pretreatment.

In several embodiments, formulations for treating malaria are provided. In one embodiment, a formulation comprising about 20%-60% (e.g. 40%) DMSO, about 5%-20% (e.g., 10%) MSM and, optionally, about 10%-40% (e.g., 20%) urea. In one embodiment, about two hundred milliliters (200 ml) are administered intravenously to malaria patients. Other amounts may also be administered. In some embodiments, an orally administered herb (e.g., qinghao, also known as sweet wormwood or *Artemisia annua*) is also administered. This treatment regime is administered a single time (or may be administered multiple times). Patients show improvements in malarial symptoms after 24 hours (e.g., reduced fever, vomiting, reduced diarrhea). In addition to the reduction in malarial symptoms, the unpleasant odor normally associated with administration of DMSO is significantly reduced.

In several embodiments, DMSO, alone or in combination with MSM, and optionally in combination with urea advantageously reduces symptoms of malaria. In some embodiments, the inclusion of a traditional medicine (such as an herb or an antibiotic) further enhances the efficacy of the formulation. As discussed above, in several embodiments DMSO, alone or in combination with MSM, functions to sensitize bacteria to a therapeutic agent. In several embodiments, subjects treated with a DMSO alone or in combination with MSM formulation include humans, non-human mammals, domesticated animals and livestock. In some embodiments, formulations disclosed herein are used to not only treat undesired symptoms and illnesses, but can also act as a preventative agent. For example, formulation may be taken on a regular basis to prevent the onset of illness (e.g., tuberculosis). In one embodiment, at risk subjects (e.g., family members or subjects who are exposed to patients having tuberculosis) will be administered lower doses of DMSO alone or in combination with MSM and antibiotics to prevent the onset of infection.

EXAMPLES

As discussed herein, MSM is used in several embodiments in conjunction with one or more antibiotics and/or DMSO in order to treat infectious diseases. The following studies were directed to determining the antimicrobial properties of both MSM and DMSO, either alone or in combination, as well as their efficacy when used in conjunction with penicillin.

The microorganisms used to test MSM, DMSO, penicillin and their combinations were *Streptococcus pyogenes* and *Streptococcus pneumonia*, based on these two organisms being responsible for a variety of human streptococcal infections. *S. pyogenes* has a hyaluronic acid capsule while *S. pneumonia* has a distinct polysaccharide capsule. The distinct carbohydrate composition of bacterial antigens found on the cell walls of these two microorganisms led *S. pyogenes* to be classified as Lancefield Group A and *S. pneumonia* to remain unclassified under Lancefield Group standards. The use of related, but structurally distinct microorganisms was intended to assist in determining if MSM, DMSO, penicillin and their combinations were more effective on one type of bacteria over the other.

Thus, the purpose of these studies was to determine 1) the antimicrobial effects of DMSO, both individually and in combination with MSM, on *S. pyogenes* and *S. pneumonia;* 2) the most effective concentrations for antimicrobial properties for such; 3) whether combining MSM and DMSO reduces the concentrations of either compound needed to achieve therapeutically relevant levels of microbial reduction; and 4) the antimicrobial effectiveness of using DMSO, and the combination of DMSO AND MSM in conjunction with an antibiotic agent.

*S. pneumonia* (#10341™) and *S. pyogenes* (#10096™) were purchased from ATCC. DMSO (#D8418) was purchased from Sigma-Aldrich. Penicillin was purchased from Henry Schein. Bacterial culture medium was purchased from Becton-Dickinson. A bioluminescent adenosine triphosphate (ATP) assay kit was purchased from Promega (#G8230).

*S. pyogenes* and *S. pneumonia* were cultured in Brain Heart Infusion media (BD 237500) at 37° C. Aliquots of the cultures were plated and exposed to the appropriate concentrations of DMSO, MSM, and/or antibiotic. Bacteria were cultured for 7 hours (for *Streptococcus pneumonia*) and 18 hours (for *Streptococcus pyogenes*) respectively. Then bacterial viability was evaluated by the Promega bioluminescent ATP assay kit. The test was conducted in triplicate.

Analysis of bacterial ATP content was used to evaluate cell viability. Bacterial ATP can be measures by direct lysis of the bacteria with a detergent, thereby releasing ATP from the cells. The released ATP reacts with user supplied luciferase and results in light emission. The intensity of the emitted light is measured with a luminometer and is proportional to the concentration of ATP. Greater concentrations of ATP are indicative of greater bacterial viability. Briefly, the reagents were prepared according the to the manufacturer's instructions. For example, opaque multiwall tubes or microplates (depending on the number of samples to be evaluated) are used to culture bacteria as discussed herein. Control tubes (culture medium without cells) are prepared to generate a value for background luminescence. Luciferase containing reagent (BacTiterGlo™) is added to each tube/well (including control tubes). After mixing thoroughly and incubating the mixture for approximately 5 minutes at room temperature, luminescence is measured using a luminometer.

For *S. pneumonia*, MSM and DMSO were prepared in concentrations of 5%, 10%, and 20%. Penicillin was prepared at concentrations of 25, 50, and 100 μg/L. For *S. pyogenes*, MSM was prepared in concentrations of 0.31, 0.63, 1.25, 2.50, 5.00, 10.0, 20.0 and tested for synergy at concentrations of 2.5, 5, and 10%; DMSO was prepared in concentrations of 0.31, 0.63, 1.25, 2.50, 5.00, 10.0, 20.0, and tested for synergy at concentrations of 2.5, 5, and 8%; and penicillin was prepared in concentrations 1.56, 3.13, 6.25, 12.5, 25.0, 50, 100

μg/L and tested for synergy at concentrations of 3.125, 6.25, and 12.5 μg/L. MSM, DMSO and penicillin were all diluted in culture medium. The synergistic effects of the various compounds in combination were then evaluated. As used herein, the term synergistic shall be given its ordinary meaning and shall also refer to instances wherein the combination of two or more substances kills a higher percentage of a microorganism than would be anticipated by adding the individual kill rates. Synergistic effects are indicated by an "*" in the Tables that follow.

Example 1

Antibacterial Effects of DMSO and MSM Alone on S. pneumonia

DMSO was added to S. pneumonia cultures to final concentrations of 5%, 10%, and 20%. At each of these concentrations, DMSO resulted in reductions in bacterial viability in a dose-dependent manner. See Table 1. Thus, in some embodiments, DMSO alone, at concentrations between 5 and 20% is effective at reducing the viability of certain bacteria. In several embodiments, DMSO also provides analgesic and/or anti-inflammatory effects, which may be beneficial, as pain and/or inflammation are associated with certain bacterial infections.

TABLE 1

Viability of S. pneumonia After DMSO Exposure

| DMSO Concentration | Viability of S. pneumonia (%) |
|---|---|
| 5 | 75.45 |
| 10 | 40.18 |
| 20 | 27.19 |

MSM alone was added to S. pneumonia cultures to final concentrations of 5%, 10%, and 20%. At each of these concentrations, MSM also resulted in reductions in bacterial viability in a dose-dependent manner. See Table 2. The extent of reduction in bacterial viability was not as robust with MSM as compared to DMSO, however, in several embodiments, MSM is still useful as an antimicrobial agent when used alone. In several embodiments, MSM alone is preferable as an antimicrobial agent because of its beneficial analgesic and anti-inflammatory properties, as both pain and inflammation may be associated with certain infections.

TABLE 2

Viability of S. pneumonia After MSM Exposure

| MSM Concentration | Viability of S. pneumonia (%) |
|---|---|
| 5 | 95.34 |
| 10 | 48.57 |
| 20 | 39.08 |

Example 2

Antibacterial Effects of Combinations of DMSO and MSM on S. pneumonia

In accordance with several embodiments described above, MSM and DMSO in combination were evaluated for their antibacterial effects on S. pneumonia. DMSO at 5%, 10%, and 20% was combined with MSM at 0% (DMSO only control), 5%, 10%, or 20%. As shown in Tables 3, 4, and 5, certain combinations of MSM with DMSO are synergistic as compared to either DMSO or MSM alone. Synergistic results as compared to DMSO or MSM alone are indicated by an "*". For example, addition of 5% MSM to 5% DMSO reduced bacterial viability to approximately 50% (see Table 3), while the combined effects of 5% MSM and 5% DMSO would be expected to be a reduction in bacterial viability to approximately 70%. Similarly, 5% MSM added to 20% DMSO reduced bacterial viability to approximately 18% (see Table 5), while combined effects of 5% MSM and 20% DMSO would be expected to be a reduction in bacterial viability to only about 22%. In contrast, 5% MSM in combination with 10% DMSO did not result in synergistic reductions in bacterial viability. Thus, the interaction of 5% MSM with DMSO exhibits a biphasic effect curve, with 5% and 20% DMSO in combination with 5% MSM resulting in unexpectedly enhanced anti-microbial effects.

These results therefore indicate that certain combinations of DMSO and MSM are more effective as antibacterial agents. Thus, in several embodiments, about 5% MSM is used in conjunction with about 5% DMSO to yield unexpected reductions in bacterial viability. In some embodiments, about 5% MSM is used in conjunction with about 20% DMSO to yield unexpected reductions in bacterial viability. Certain such embodiments are particularly advantageous because both DMSO and MSM have analgesic and anti-inflammatory properties, both of which may be beneficial in reducing symptoms of certain microbial infections. Moreover, in some embodiments employing a larger (e.g., 20%) concentration of DMSO, the MSM in the formulation functions to reduce one or more of the side effects of DMSO (e.g., odor associated with DMSO administration). In still additional embodiments, those combinations that show synergy in reducing microbial viability also reduce the amount of time for the compounds to affect viability. In some embodiments, such effects reduce the overall treatment time (e.g., complete resolution of an infection) and/or reduce the time to demonstrable improvements in symptoms (e.g., reduced time to apyresis). In still additional embodiments, those combinations of DMSO and MSM that did not demonstrate synergistic effects on bacterial viability may still beneficially (and synergistically) impact treatment times. In some embodiments, as discussed below, certain combinations of MSM and DMSO render another agent more efficacious (e.g., same effects at a lower administered dose).

TABLE 3

Viability of S. pneumonia After Exposure to Various Concentrations of MSM in 5% DMSO

| DMSO (%) | MSM (%) | S. pneumonia viability (%) |
|---|---|---|
| 5 | 0 | 75.45 |
| 5 | 5 | 50.94* |
| 5 | 10 | 45.40 |
| 5 | 20 | 27.22 |

TABLE 4

Viability of S. pneumonia After Exposure to Various Concentrations of MSM in 10% DMSO

| DMSO (%) | MSM (%) | S. pneumonia viability (%) |
|---|---|---|
| 10 | 0 | 40.18 |
| 10 | 5 | 47.81 |
| 10 | 10 | 37.42 |
| 10 | 20 | 11.95 |

TABLE 5

Viability of *S. pneumonia* After Exposure
to Various Concentrations of MSM in 20% DMSO

| DMSO (%) | MSM (%) | *S. pneumonia* viability (%) |
|---|---|---|
| 20 | 0 | 27.19 |
| 20 | 5 | 17.60* |
| 20 | 10 | 7.76 |
| 20 | 20 | 5.15 |

Example 3

Antibacterial Effects of DMSO Alone or in Combination with MSM in Further Combination with Penicillin on *S. pneumonia*

As discussed herein, in several embodiments, the addition of DMSO alone or in combination with MSM to a therapeutic agent, such as an antibiotic, acts to reduce the effective concentration of the therapeutic agent. For example, in some embodiments, DMSO alone or in combination with MSM in combination with an antibiotic reduces the amount of antibiotic needed to achieve reductions in the viability of target bacteria. In some embodiments, the amount of penicillin, or another beta-lactam antibiotic needed for efficacious reduction in bacterial viability is reduced. In other embodiments, other antibiotics with other mechanisms of action (e.g., aminoglycosides, tetracyclines, macrolides, among others) are needed in reduced concentrations. In some embodiments, the reduction of the amount of antibiotic (or other therapeutic agent) needed for an effect also reduces one or more side effects associated with the agent. For example, some antibiotic agents are associated with gastric discomfort and/or diarrhea, due to the reduced viability of native gastrointestinal flora. Other antibiotics have side effects such as reduced appetite, dry mouth, and the like. In some instances, the route of delivery, as discussed above, can be used to partially manage the side effects. However, in some embodiments, reduction in the amount of drug needed for efficacious treatment is more advantageous in reducing side effects. Additionally, in some embodiments, the reduction in the amount of antibiotic agent required to reduce microbial viability reduces the incidence of allergic events induced by the antibiotic. Moreover, the reduction in amount of agent needed for therapy, in some embodiments, increases the number of doses (and therefore possibly the number of patients) that may be treated with a given amount of agent.

DMSO in Combination with Penicillin

DMSO, at 0, 5, 10, or 20% was individually combined with 25, 50, or 100 µg/L penicillin and the combinations were evaluated for their effects on bacterial viability. As shown in Tables 6-8, no synergistic reductions in bacterial viability were detected with any combinations of varying DMSO concentrations and varying penicillin concentrations. As discussed above however, these combinations, in some embodiments, may still be effective at reducing the treatment time (either to resolution or to reduction of symptoms). These data do indicate, however, that certain combinations of DMSO and penicillin result in equally efficacious reductions in bacterial viability, with a decreased amount of penicillin (e.g., DMSO functioning to reduce the effective concentration of penicillin).

For example, 20% DMSO in combination with 100 µg/L penicillin yielded approximately 80% reduction in bacterial viability (21.76% viability, see Table 8). 20% DMSO in combination with 50 µg/L penicillin also reduced bacterial viability by about 80% (19.14% viability, see Table 7). Finally, 20% DMSO in combination with only 25 µg/L penicillin still reduced bacterial viability by 78% (22.08% viability, see Table 6). Thus, when combined with 20% DMSO, the effective concentration of penicillin can be reduced by 5-fold, while still achieving the same reduction in bacterial viability. As discussed above, this type of synergy is particularly advantageous in some embodiments, as the incidence of allergic reactions to an antibiotic agent may be reduced due to the lower concentration of antibiotic needed. Moreover, in some such embodiments, the rate of generation of microbial resistance may be reduced, again due to the reduction in the necessary amount of antibiotic. In some embodiments, the reduced amount of antibiotic also reduces the incidence of antibiotic related side effects. In still additional embodiments, despite the reduction in the amount of antibiotic required to reach a given therapeutic effect, the time to reach that therapeutic effect is reduced (e.g., treatment time reduced from weeks to days). Additionally, a given amount of penicillin may be used to treat a greater number of patients (or a single patient a greater number of times). This may be of particular importance in remote locations, where transport and/or storage of a drug is more difficult In some embodiments, the penetrant nature of DMSO functions to increase the amount of penicillin able to enter the bacterial wall and inhibit formation of peptidoglycan cross-links. Likewise, in other embodiments, DMSO allows other antibacterial or therapeutic agents (e.g., non beta-lactam antibiotics) greater access to the interior of the bacteria, enhancing the efficacy of the antibiotic. In some embodiments, the DMSO provides favorable effects for a patient, such as, pain reduction, anti-inflammatory effects, and the like.

Similar trends are present in the when 10% and 5% DMSO is combined with penicillin, in that similar reductions in bacterial efficiency are achieved, despite using lower concentrations of penicillin (see e.g., 10% and 5% data points in Tables 6-8). In some embodiments, reduced comparative efficacy of the 10% or 5% DMSO/penicillin combinations is not of clinical significance (e.g., for treatment of a low grade, non-emergency infection). As such, despite the lesser overall reduction in bacterial viability, combinations of 10% or 5% DMSO with penicillin are preferred in some embodiments. In such embodiments, the reduced amount of DMSO may be advantageous, in that DMSO-associated side effects may be reduced (e.g., skin or mucous membrane irritation; odor associated with administration).

TABLE 6

*S. pneumonia* Viability After Exposure
to Various Concentrations of Penicillin

| Penicillin (µg/L) | *S. pneumonia* viability (%) |
|---|---|
| 25 | 79.82 |
| 50 | 42.70 |
| 100 | 40.93 |

TABLE 7

*S. pneumonia* Viability After Exposure to 25 µg/L
of Penicillin with Various Concentrations of DMSO

| Penicillin (µg/L) | DMSO (%) | *S. pneumonia* viability (%) |
|---|---|---|
| 25 | 0 | 79.82 |
| 25 | 5 | 46.13 |

TABLE 7-continued

S. pneumonia Viability After Exposure to 25 μg/L
of Penicillin with Various Concentrations of DMSO

| Penicillin (μg/L) | DMSO (%) | S. pneumonia viability (%) |
|---|---|---|
| 25 | 10 | 39.78 |
| 25 | 20 | 22.08 |

TABLE 8

S. pneumonia Viability After Exposure to 50 μg/L
of Penicillin with Various Concentrations of DMSO

| Penicillin (μg/L) | DMSO (%) | S. pneumonia viability (%) |
|---|---|---|
| 50 | 0 | 42.70 |
| 50 | 5 | 46.27 |
| 50 | 10 | 37.09 |
| 50 | 20 | 19.14 |

TABLE 9

S. pneumonia Viability After Exposure to 100 μg/L
of Penicillin with Various Concentrations of DMSO

| Penicillin (μg/L) | DMSO (%) | S. pneumonia viability (%) |
|---|---|---|
| 100 | 0 | 40.93 |
| 100 | 5 | 45.09 |
| 100 | 10 | 35.80 |
| 100 | 20 | 21.76 |

TABLE 10

S. pneumonia Viability After Exposure to 25 μg/L
of Penicillin with Various Concentrations of MSM

| Penicillin (μg/L) | MSM (%) | S. pneumonia viability (%) |
|---|---|---|
| 25 | 0 | 79.82 |
| 25 | 5 | 41.23* |
| 25 | 10 | 41.83 |
| 25 | 20 | 25.36 |

TABLE 11

S. pneumonia Viability After Exposure to 50 μg/L
of Penicillin with Various Concentrations of MSM

| Penicillin (μg/L) | MSM (%) | S. pneumonia viability (%) |
|---|---|---|
| 50 | 0 | 42.70 |
| 50 | 5 | 41.23 |
| 50 | 10 | 47.47 |
| 50 | 20 | 20.75 |

TABLE 12

S. pneumonia Viability After Exposure to 100 μg/L
of Penicillin with Various Concentrations of MSM

| Penicillin (μg/L) | MSM (%) | S. pneumonia viability |
|---|---|---|
| 100 | 0 | 40.93 |
| 100 | 5 | 41.75 |
| 100 | 10 | 36.67 |
| 100 | 20 | 21.37 |

MSM in Combination with Penicillin

The combination of 5% MSM with 25 μg/L of penicillin exhibited a synergistic reduction in the viability of S. pneumonia, leading to only 41% viability (see Table 10). Synergy as compared to the expected results based on MSM alone and penicillin alone is indicated in the Tables by an "*". In contrast, 5% MSM alone reduced viability by only ~5%, while 25 μg/L penicillin alone reduced viability by ~21%. Thus, the 5% MSM/25 μg/L of penicillin combination is unexpectedly more efficacious than expected based on the results obtained with MSM or penicillin alone.

Moreover, as with DMSO, certain concentrations of MSM allowed lower concentrations of penicillin to reduce bacterial viability nearly as effectively as higher concentrations. For example, 20% MSM with 100 μg/L penicillin reduced S. pneumonia viability to 21.37%, (see Table 12) 20% MSM with 50 μg/L penicillin reduced S. pneumonia viability to 20.75% (see Table 11). Thus, with use of 20% MSM, the required concentration of penicillin is reduced by one-half. Continuing this trend is the combination of 20% MSM with 25 μg/L penicillin reduced S. pneumonia viability to approximately 25% (see Table 10). Thus, in some embodiments, if antibiotic related side effects are of concern, certain concentrations of MSM are unexpectedly advantageous in allowing reduced levels of antibiotic to be administered. Similarly, though with a less robust reduction in bacterial viability, 5% MSM allowed 25 μg/L penicillin to perform nearly identically to 100 μg/L penicillin (compare Tables 10-12 for 25 μg/L penicillin).

Example 4

Antibacterial Effects of DMSO and MSM in Combination with Penicillin on S. pneumonia Based on the synergistic results seen in certain combinations of MSM or DMSO with penicillin, the present experiment was performed in order to identify the various combinations of MSM, DMSO, and penicillin that yielded synergistic reductions in bacterial viability as compared to combination the effects of combining DMSO, MSM, and penicillin on bacterial viability. This experiment was also designed to identify combinations of the three compounds that advantageously allow one or more of the compounds to be reduced, yet still efficaciously reduce bacterial viability.

DMSO at 5, 10, and 20% was combined individually with MSM at one of 5, 10, or 20% and penicillin at one of 25, 50, or 100 μg/L. Viability was assessed as described above. Viability data are presented in Table 13. The "*" symbol represents synergistic results as compared to the corresponding combination of DMSO and penicillin. The "ψ" symbol represents synergistic results as compared to the corresponding combination of MSM and penicillin. The values for the reduction in bacterial viability were added together to determine the threshold reduction for synergy. For example, 5% DMSO reduces viability by approximately 25% and 25 μg/L penicillin reduced viability by approximately 21%, for a total combined reduction expected of approximately 46%. This represents a 64% viability. Thus, if the combination of 5% MSM, 5% DMSO, and 25 μg/L penicillin results in less than 64% viability, synergy between the compounds has been identified.

Several combinations of MSM, DMSO, and penicillin yield synergistic improvements in bacterial reduction. For example, the combination of 5% DMSO, 5% MSM, and 25 μg/L penicillin reduced bacterial viability to approximately 52% (see Table 13). 5% DMSO in combination with 25 μg/L penicillin reduced bacteria viability to approximately 64% (e.g., about a 46% reduction, based on the individual reduction seen with 5% DMSO, see Table 1, and the individual reduction seen with 25 μg/L penicillin, see Table 5). Thus the combination of all three compounds reduced bacterial viability by about an additional 12%. Similarly, the combination of 5% MSM with 25 μg/L penicillin resulted in bacteria viability of about 74%, while the combination of all three compounds reduced viability by nearly an additional 22%.

In some combinations, synergistic results were detected with respect to both DMSO and penicillin as well as MSM plus penicillin. For example, 10% DMSO in combination with 20% MSM and 25 μg/L penicillin is yielded a synergistic improved in antimicrobial activity as compared to both reference combinations. Thus in some embodiments, the combination of all three compounds outperforms DMSO plus penicillin and MSM plus penicillin. In some embodiments, such combinations are particularly advantageous in combating infections, due to their unexpected efficacy. As such, those combinations, in some embodiments, result in a more rapid, more complete, or more effective reduction and/or elimination of an unwanted bacterial infection.

In other combinations, synergy was detected only with respect to either DMSO plus penicillin or MSM plus penicillin. For example, the combination of 5% MSM with 10% DMSO and 25 μg/L penicillin was synergistic with respect to MSM plus penicillin, but not with respect to DMSO plus penicillin. In some embodiments, such information is useful, for example if an individual is sensitive to one of the three compounds, it may be that the offending compound can be removed from the combination, but effective treatment can still result with only two compounds. In other embodiments, the differential synergy is due to the highly effective nature of one or more of the compounds when used alone. As a result, synergy may be mathematically impossible. As discussed above, in some such embodiments, the combination of all three compounds increases rate of reduction in bacterial viability and increases the duration of reduction (e.g., prevents regrowth and/or reinfection). Thus, even when a synergistic reduction in the overall viability of bacteria is not recognizable, in certain embodiments, other synergistic results are still detectable.

In addition to the synergistic effects discussed above, there are several instances wherein the certain combinations of DMSO, MSM and penicillin allow for a reduction in the efficacious concentration of penicillin. For example, as shown in Table 13, the combination of 5% DMSO with 20% MSM yields very similar overall bacterial viability over the range of penicillin concentrations tested (from ~25% viability with 25 μg/L penicillin to ~18% viability with 100 μg/L penicillin). Additionally, 10% DMSO with 20% MSM resulted in nearly identical bacterial viabilities across the penicillin concentration range.

Similar results are seen with 20% DMSO in combination with 5, 10, or 20% MSM and any concentration of penicillin. These results reveal a slightly wider range of bacterial viability across the different penicillin concentrations, however, given that the reduction in all cases approaches approximately 90 to 95%, these combinations are all still very effective.

In some embodiments, therefore, certain combinations of DMSO and MSM allow for the reduction in penicillin concentrations. In some embodiments, the presence of 20% MSM allows penicillin to be reduced while significant bacterial reductions are realized. In other embodiments, the presence of 20% DMSO allows penicillin to be reduced while significant bacterial reductions are realized. In still additional embodiments, the presence of 20% MSM and 20% DMSO allows penicillin to be reduced while significant bacterial reductions are realized. These embodiments are particularly advantages in avoiding complications due to adverse reactions to penicillin (e.g., allergies, side effects, etc.) Thus in some embodiments, methods for reducing side-effects or adverse reactions to an antibiotic are provided. In some embodiments, 20% MSM, 20% DMSO, or 20% MSM and 20% DMSO reduce the effective concentration of antibiotic required to generate a therapeutic reduction in bacterial viability. In still additional embodiments, other aspects of reducing bacterial viability are maintained (and/or improved) even with a reduction in the amount of penicillin (e.g., the rate of reduction in bacterial viability, the duration of reduction, etc.).

TABLE 13

S. pneumonia Viability After Exposure to Various combinations of DMSO, MSM, and Penicillin

| DMSO (%) | MSM (%) | Penicillin (μg/L) | S. pneumonia viability (%) |
|---|---|---|---|
| 5 | 5 | 25 | 52.11*,Ψ |
| 5 | 5 | 50 | 43.36 |
| 5 | 5 | 100 | 53.03 |
| 5 | 10 | 25 | 51.82* |
| 5 | 10 | 50 | 44.52 |
| 5 | 10 | 100 | 31.33 |
| 5 | 20 | 25 | 24.91* |
| 5 | 20 | 50 | 19.20 |
| 5 | 20 | 100 | 18.12 |
| 10 | 5 | 25 | 44.41Ψ |
| 10 | 5 | 50 | 38.24 |
| 10 | 5 | 100 | 36.19 |
| 10 | 10 | 25 | 39.38 |
| 10 | 10 | 50 | 33.73 |
| 10 | 10 | 100 | 25.98 |
| 10 | 20 | 25 | 11.87*,Ψ |
| 10 | 20 | 50 | 11.03 |
| 10 | 20 | 100 | 10.96 |
| 20 | 5 | 25 | 12.74*,Ψ |
| 20 | 5 | 50 | 13.39Ψ |
| 20 | 5 | 100 | 9.28Ψ |
| 20 | 10 | 25 | 7.69*,Ψ |
| 20 | 10 | 50 | 7.74 |
| 20 | 10 | 100 | 5.58 |
| 20 | 20 | 25 | 4.93*,Ψ |
| 20 | 20 | 50 | 5.60 |
| 20 | 20 | 100 | 1.80 |

Example 5

Antibacterial Effects of DMSO and MSM Alone on S. pyogenes

As discussed above, the structure of S. pyogenes differs from that of S. pneumonia, and therefore additional experiments were undertaken to evaluate the synergistic effects of various concentrations of DMSO and MSM, as well as combinations of DMSO, MSM, and penicillin.

DMSO was added to S. pyogenes cultures to final concentrations of 0.31, 0.63, 1.25, 2.50, 5.00, 10.0, or 20.0%. At these concentrations, DMSO resulted in reductions in bacterial viability in a dose-dependent manner. See Table 14. Thus, in some embodiments, DMSO alone, at concentrations between 5 and 20% is effective at reducing the viability of certain bacteria. In several embodiments, DMSO also provides analgesic and/or anti-inflammatory effects, which may be beneficial, as pain and/or inflammation are associated with certain bacterial infections.

MSM alone was added to *S. pyogenes* cultures to final concentrations of 0.31, 0.63, 1.25, 2.50, 5.00, 10.0, or 20.0%. At these concentrations, MSM also resulted in reductions in bacterial viability in a dose-dependent manner. See Table 15. Thus, in some embodiments, MSM alone, at concentrations between 5 and 20% is effective at reducing the viability of certain bacteria. In several embodiments, MSM also provides analgesic and/or anti-inflammatory effects, which may be beneficial, as pain and/or inflammation are associated with certain bacterial infections.

TABLE 14

Viability of *S. pyogenes* After DMSO Exposure

| DMSO Concentration | Viability of *S. pyogenes* (%) |
| --- | --- |
| 0.31 | 100 |
| 0.63 | 100 |
| 1.25 | 100 |
| 2.50 | 100 |
| 5.00 | 96.66 |
| 10.0 | 14.50 |
| 20.0 | 5.14 |

TABLE 15

Viability of *S. pyogenes* After MSM Exposure

| MSM Concentration | Viability of *S. pyogenes* (%) |
| --- | --- |
| 0.31 | 100 |
| 0.63 | 100 |
| 1.25 | 100 |
| 2.50 | 100 |
| 5.00 | 95.88 |
| 10.0 | 23.94 |
| 20.0 | 15.18 |

Example 6

Antibacterial Effects of DMSO and MSM in Combination on *S. pyogenes*

In accordance with several embodiments described above, MSM and DMSO in combination were evaluated for their antibacterial effects on *S. pyogenes*. DMSO at 2.5%, 5%, and 8% was combined with MSM at 0% (DMSO only control), 2.5%, 5%, and 10%. As shown in Tables 16, 17, and 18 certain combinations of MSM with DMSO are synergistic as compared to the effects of either DMSO or MSM alone. Synergistic results as compared to DMSO or MSM alone are indicated by an "*". For example, addition of 2.5% MSM to 2.5% DMSO reduced bacterial viability to approximately 65% (see Table 16), while the no effect of these concentrations of MSM and DMSO would be expected, as individually, neither compound reduced bacterial viability. The synergistic effect is also seen with 2.5% DMSO and 5% MSM, where bacterial viability is reduced by nearly 83% (as compared to an expected 4% reduction based on the compounds' effects alone). Synergy is also seen with 5% DMSO in combination with any concentration of MSM. Thus, in some embodiments, DMSO at 5% induces synergistic reductions in bacterial viability in combination with any concentration of MSM between 2.5% and 10%. In some embodiments, DMSO at 2.5% and MSM in concentrations between 2.5% and 5% are advantageously and unexpectedly synergistic at reducing bacteria viability.

TABLE 16

Viability of *S. pyogenes* After Exposure to Various Concentrations of MSM in 2.5 DMSO

| DMSO (%) | MSM (%) | *S. pyogenes* viability (%) |
| --- | --- | --- |
| 2.5 | 0 | 100 |
| 2.5 | 2.5 | 65.06* |
| 2.5 | 5.0 | 17.71* |
| 2.5 | 10.0 | 16.37 |

TABLE 17

Viability of *S. pyogenes* After Exposure to Various Concentrations of MSM in 5 DMSO

| DMSO (%) | MSM (%) | *S. pyogenes* viability (%) |
| --- | --- | --- |
| 5.0 | 0 | 96.66 |
| 5.0 | 2.5 | 36.21* |
| 5.0 | 5.0 | 7.87* |
| 5.0 | 10.0 | 7.64* |

TABLE 18

Viability of *S. pyogenes* After Exposure to Various Concentrations of MSM in 8 DMSO

| DMSO (%) | MSM (%) | *S. pyogenes* viability (%) |
| --- | --- | --- |
| 8.0 | 0 | 9.96 |
| 8.0 | 2.5 | 14.37 |
| 8.0 | 5.0 | 5.97 |
| 8.0 | 10.0 | 5.60 |

Example 7

Antibacterial Effects of DMSO or MSM in Combination with Penicillin on *S. pyogenes*

Various concentrations of penicillin alone were evaluated for their ability to reduce viability of *S. pyogenes*. As shown in Table 19, penicillin decreased bacterial viability in a dose-dependent fashion.

TABLE 19

*S pyogenes* Viability After Exposure to Various Concentrations of Penicillin

| Penicillin (µg/L) | *S. pyogenes* viability (%) |
| --- | --- |
| 1.56 | 100 |
| 3.13 | 100 |
| 6.25 | 100 |
| 12.5 | 13.16 |
| 25.0 | 9.07 |
| 50 | 9.57 |
| 100 | 9.40 |

DMSO in Combination with Penicillin

Due to the highly efficacious nature of penicillin concentrations at or above 25 µg/L, DMSO was combined with concentrations of penicillin that were less efficacious (ranging from 3.125 to 12.5 µg/L). As such, identification of synergism between DMSO and penicillin would be less likely to be mathematically obscured.

As shown in Tables 20, 21, and 22 (identified by an "*") several combinations of DMSO and penicillin resulted in synergistic results. For example, 5% DMSO in combination with 3.125 µg/L penicillin, based on the efficacy of the two compounds alone, would only be expected to reduce bacteria viability by about 4%. However, when combined, the actual reduction was approximately 10-fold greater (viability reduced to ~61%, see Table 20). Similar synergistic effects were seen when 5% DMSO was combined with 6.25 µg/L or 12.5 µg/L penicillin (see Table 21 and 22, respectively). Thus, in several embodiments, combinations of DMSO and penicillin that, taken alone are ineffective, unexpectedly reduce bacterial viability. Such embodiments are particularly advantageous in that they may allow for treatment of a patient that was thought to be refractory to the individual compounds. Moreover, substantial synergy is detected after combining relatively low concentrations of each of the two compounds. As such, side-effects may be minimized.

In the event that side effects are at issue, certain embodiments allow the reduction of one or more of the compounds while still retaining a relatively efficacious effect on bacterial viability. For example, if side-effects from DMSO are experienced, a concentration of 12.5 µg/L penicillin in combination with 5% DMSO (a 3% reduction in DMSO) still reduces bacterial viability to approximately 15% of the starting population. Similarly, if penicillin presents issues, the combination of 8% DMSO with 6.25 µg/L penicillin is virtually indistinguishable from 8% DMSO with 12.5 µg/L penicillin. Thus, penicillin concentrations can be reduced by 50%, while efficacy is retained. Similar results occur with 5% DMSO and 6.25 µg/L penicillin. Thus, in some embodiments, there are provided methods and compositions for reducing the efficacious concentration of DMSO and/or penicillin.

TABLE 20

S pyogenes Viability After Exposure to 3.13 µg/L
of Penicillin with Various Concentrations of DMSO

| Penicillin (µg/L) | DMSO (%) | S. pyogenes viability (%) |
|---|---|---|
| 3.13 | 0 | 100 |
| 3.13 | 2.5 | 100 |
| 3.13 | 5.0 | 60.85* |
| 3.13 | 8.0 | 12.90 |

TABLE 21

S pyogenes Viability After Exposure to 6.25 µg/L
of Penicillin with Various Concentrations of DMSO

| Penicillin (µg/L) | DMSO (%) | S. pyogenes viability (%) |
|---|---|---|
| 6.25 | 0 | 100 |
| 6.25 | 2.5 | 100 |
| 6.25 | 5.0 | 60.23* |
| 6.25 | 8.0 | 6.91* |

TABLE 22

S pyogenes Viability After Exposure to 12.5 µg/L
of Penicillin with Various Concentrations of DMSO

| Penicillin (µg/L) | DMSO (%) | S. pyogenes viability (%) |
|---|---|---|
| 12.5 | 0 | 13.16 |
| 12.5 | 2.5 | 19.63 |
| 12.5 | 5.0 | 14.77* |
| 12.5 | 8.0 | 6.43 |

MSM in Combination with Penicillin

Similar experiments to those using DMSO were performed by combining MSM with penicillin ranging from 3.125 to 12.5 µg/L. Results are shown in Tables 23, 24, and 25. Synergy is indicated by an "*". The reduction in bacterial viability due to MSM alone at 8% has been estimated to be approximately 89%. As with DMSO, previously ineffective concentrations of MSM and penicillin were effective in combination at reducing bacterial viability. When taken alone, no effect would be expected from 3.13 µg/L penicillin with 2.5% MSM, however an 8% reduction in viability is detected (see Table 23). These effects are more pronounced with the combination of 6.25 µg/L penicillin with MSM. For example, 5% MSM with 6.25 µg/L penicillin would be expected to yield a 96% viable bacterial population (see table 24). However, data indicate that viability was reduced to about 17%, nearly an 80% reduction from expected results. Synergy was not detected when 12.5 µg/L penicillin was used, due to the efficacy of that concentration of penicillin alone. Thus, in some embodiments, MSM in concentrations between 2.5% and 8%, when combined with penicillin in concentrations of 3.125 to 6.25 µg/L result in synergistic decreases in bacterial viability. In several embodiments, previously ineffective concentrations of the compound are efficacious when combined.

TABLE 23

S pyogenes Viability After Exposure to 3.13 µg/L
of Penicillin with Various Concentrations of MSM

| Penicillin (µg/L) | MSM (%) | S. pyogenes viability (%) |
|---|---|---|
| 3.13 | 0 | 100 |
| 3.13 | 2.5 | 92.89* |
| 3.13 | 5.0 | 78.31* |
| 3.13 | 8.0 | 9.91* |

TABLE 24

S pyogenes Viability After Exposure to 6.25 µg/L
of Penicillin with Various Concentrations of MSM

| Penicillin (µg/L) | MSM (%) | S. pyogenes viability (%) |
|---|---|---|
| 6.25 | 0 | 100 |
| 6.25 | 2.5 | 90.11* |
| 6.25 | 5.0 | 17.42* |
| 6.25 | 8.0 | 10.77* |

TABLE 25

S pyogenes Viability After Exposure to 12.5 µg/L
of Penicillin with Various Concentrations of MSM

| Penicillin (µg/L) | MSM (%) | S. pyogenes viability (%) |
|---|---|---|
| 12.5 | 0 | 13.16 |
| 12.5 | 2.5 | 16.33 |
| 12.5 | 5.0 | 12.85 |
| 12.5 | 8.0 | 16.02 |

Example 8

Antibacterial Effects of DMSO and MSM in Combination with Penicillin on S. pyogenes As with S. pneumonia, combinations of various concentrations of DMSO, MSM, and penicillin were evaluated for their effects on bacterial viability and possible synergistic activity as compared to MSM with penicillin or DMSO with pencillin. Results are shown in Table 26. Synergy as compared to DMSO and penicillin is indicated by an "*" while synergy as compared to MSM and penicillin is indicated by an "ψ". As can be seen by the data in Table 26, substantial synergy was detected across the various concentrations of compounds. Most combinations of DMSO and MSM exhibited a dose-response curve based on the concentration of penicillin used. Based on the efficacy of 12.5 μg/L alone, it is not unexpected that combinations of this concentration of penicillin with DMSO and MSM should be more effective. Of interest, the previously ineffective concentrations of pencillin are rendered effective in a dose dependent manner by combination with DMSO and MSM. For example, 2.5% DMSO with 5% MSM and 3.125 μg/L pencillin would be expected to reduce bacterial viability to between 100% and 96% (when compared to DMSO+penicillin and MSM+penicillin, respectively). However, the combination of all three reduced bacterial viability to about 19%. The expected results are similar for combinations with 6.25 μg/L penicillin, but the actual combination reduced bacterial viability even further, to about 13%. Thus, in some embodiments, it appears that certain concentrations of DMSO and MSM work as bacterial sensitizers, allowing lower concentrations of penicillin to function in a dose-dependent manner, as if they were in fact higher concentrations of penicillin. Thus in some embodiments, certain combinations of DMSO, MSM, and penicillin are advantageous because they render a previously inactive set of individual compounds active against bacterial viability.

In some embodiments, simply increasing concentrations of the various compounds does not result larger reductions in bacterial viability. For example, the combination of 8% DMSO with 2.5% MSM and 3.125 μg/L penicillin appears to be more effective than 8% DMSO with 2.5% MSM and 12.5 μg/L penicillin. Thus, in several embodiments, precise combinations of each of the three compounds are used to maximize the reduction in bacterial viability. For example, in some embodiments, 2.5% to 5% DMSO in combination with 2.5, 5, or 20% MSM and with 3.125, 6.25, or 12.5 μg/L penicillin results in synsergistic effects with respect to bacterial viability reduction. In one embodiment, 8% DMSO is used, wherein MSM is provided at 2.5% and penicillin is present at 3.125 μg/L. However, increasing either the MSM or penicillin when used with 8% DMSO reduces the overall efficacy of the combination.

TABLE 26

S. pneumonia Viability After Exposure to Various combinations of DMSO, MSM, and Penicillin

| DMSO (%) | MSM (%) | Penicillin (μg/L) | S. pyogenes viability (%) |
|---|---|---|---|
| 2.5 | 2.5 | 3.125 | 91.74*,ψ |
| 2.5 | 2.5 | 6.25 | 60.55*,ψ |
| 2.5 | 2.5 | 12.5 | 8.08*,ψ |
| 2.5 | 5 | 3.125 | 18.72*,ψ |
| 2.5 | 5 | 6.25 | 13.38*,ψ |

TABLE 26-continued

S. pneumonia Viability After Exposure to Various combinations of DMSO, MSM, and Penicillin

| DMSO (%) | MSM (%) | Penicillin (μg/L) | S. pyogenes viability (%) |
|---|---|---|---|
| 2.5 | 5 | 12.5 | 9.41* |
| 2.5 | 10 | 3.125 | 16.05*,ψ |
| 2.5 | 10 | 6.25 | 11.78*,ψ |
| 2.5 | 10 | 12.5 | 11.77* |
| 5 | 2.5 | 3.125 | 14.60*,ψ |
| 5 | 2.5 | 6.25 | 10.44*,ψ |
| 5 | 2.5 | 12.5 | 9.55*,ψ |
| 8 | 2.5 | 3.125 | 9.55*,ψ |
| 8 | 2.5 | 6.25 | 10.28ψ |
| 8 | 2.5 | 12.5 | 15.55ψ |

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of sensitizing a drug resistant bacterial microorganism that does not cause tuberculosis to the drug to which the microorganism is resistant, comprising:
   contacting the microorganism with a formulation comprising 5-15% methylsulfonylmethane (MSM); and
   contacting the microorganism with the drug to which the bacterial microorganism is resistant,
thereby sensitizing the drug resistant bacterial microorganism to the drug, wherein the microorganism is methicillin-resistant Staphylococcus aureus (MRSA) and the drug is methicillin.

2. The method of claim 1, wherein the microorganism is contacted with the MSM before the microorganism is contacted with the drug.

3. The method of claim 1, wherein the microorganism is contacted with the MSM at the same time that the microorganism is contacted with the drug.

4. The method of claim 1, wherein the microorganism is contacted with a formulation comprising 7-15% MSM.

5. The method of claim 1, wherein the formulation further comprises no more than 0.63% dimethylsulfoxide (DMSO).

6. The method of claim 4, wherein the formulation comprises 7% MSM.

7. The method of claim 4, wherein the formulation comprises 10% MSM.

8. The method of claim 4, wherein the formulation comprises 15% MSM.

9. The method of claim 1, wherein contacting the microorganism with the formulation comprising 5-15% MSM, the drug, or both, occurs is in a subject.

10. The method of claim 9, wherein the microorganism is methicillin-resistant Staphylococcus aureus (MRSA).

11. The method of claim 9, wherein the MSM is administered topically.

12. The method of claim 9, wherein the MSM is administered by inhalation.

* * * * *